United States Patent
Koob

(10) Patent No.: US 11,589,973 B2
(45) Date of Patent: Feb. 28, 2023

(54) METHODS OF MAKING COLLAGEN FIBER MEDICAL CONSTRUCTS AND RELATED MEDICAL CONSTRUCTS, INCLUDING PATCHES

(71) Applicant: MiMedx Group, Inc., Marietta, GA (US)

(72) Inventor: Thomas J. Koob, Kennesaw, GA (US)

(73) Assignee: MiMedx Group, Inc., Marietta, GA (US)

( * ) Notice: Subject to any disclaimer, the term of this patent is extended or adjusted under 35 U.S.C. 154(b) by 937 days.

(21) Appl. No.: 16/410,360

(22) Filed: May 13, 2019

(65) Prior Publication Data
US 2019/0350690 A1 Nov. 21, 2019

Related U.S. Application Data

(60) Provisional application No. 62/672,136, filed on May 16, 2018.

(51) Int. Cl.
| | |
|---|---|
| *A61F 2/00* | (2006.01) |
| *A61L 31/04* | (2006.01) |
| *B29C 53/56* | (2006.01) |
| *B29C 53/00* | (2006.01) |
| *A61F 13/00* | (2006.01) |
| *B29L 31/00* | (2006.01) |

(52) U.S. Cl.
CPC ...... *A61F 2/0063* (2013.01); *A61F 13/00008* (2013.01); *A61L 31/044* (2013.01); *B29C 53/005* (2013.01); *B29C 53/56* (2013.01); *A61F 2002/0068* (2013.01); *A61F 2220/0008* (2013.01); *A61F 2240/001* (2013.01); *B29K 2089/00* (2013.01); *B29K 2995/0056* (2013.01); *B29L 2031/753* (2013.01)

(58) Field of Classification Search
CPC .............. A61F 2/0063; A61F 13/00008; A61F 2002/0068; A61F 2220/0008; A61F 2240/001; A61L 31/044; A61L 27/24; B29C 53/005; B29C 53/56; B29K 2089/00; B29K 2995/0056; B29L 2031/753

See application file for complete search history.

(56) References Cited

U.S. PATENT DOCUMENTS

| | | |
|---|---|---|
| 4,979,956 A | 12/1990 | Silvestrini |
| 6,565,960 B2 | 5/2003 | Koob et al. |
| 6,821,530 B2 | 11/2004 | Koob et al. |
| 8,367,148 B2 | 2/2013 | Greenhalgh et al. |
| 9,078,775 B2 | 7/2015 | Li et al. |
| 9,125,759 B2 | 9/2015 | Greenhalgh et al. |
| 2002/0095218 A1 | 7/2002 | Carr, Jr. et al. |
| 2006/0167561 A1 | 7/2006 | Odar et al. |
| 2008/0051834 A1 | 2/2008 | Mazzocca et al. |
| 2008/0188933 A1 | 8/2008 | Koob et al. |
| 2009/0105753 A1 | 4/2009 | Greenhalgh et al. |

(Continued)

*Primary Examiner* — Yashita Sharma
(74) *Attorney, Agent, or Firm* — Myers Bigel, P.A.

(57) ABSTRACT

Implantable medical constructs formed by winding using winding support structures that can be flexible and can be integrated into the medical construct with biocompatible fiber(s) and/or yarn(s) and at least one continuous length collagen fiber. The implantable medical construct can include open suture anchor apertures formed using posts during a winding sequence.

8 Claims, 30 Drawing Sheets
(7 of 30 Drawing Sheet(s) Filed in Color)

(56) References Cited

U.S. PATENT DOCUMENTS

| | | |
|---|---|---|
| 2011/0054524 A1 | 3/2011 | Beevers et al. |
| 2011/0190795 A1* | 8/2011 | Hotter ................... A61F 2/0063 606/151 |
| 2012/0022646 A1* | 1/2012 | Mortarino ............. A61F 2/0063 623/8 |
| 2015/0283305 A1 | 10/2015 | Li et al. |
| 2017/0014130 A1* | 1/2017 | Patenaude ............ A61B 17/085 |
| 2017/0042683 A1* | 2/2017 | Hansen ..................... A61F 2/32 |

* cited by examiner

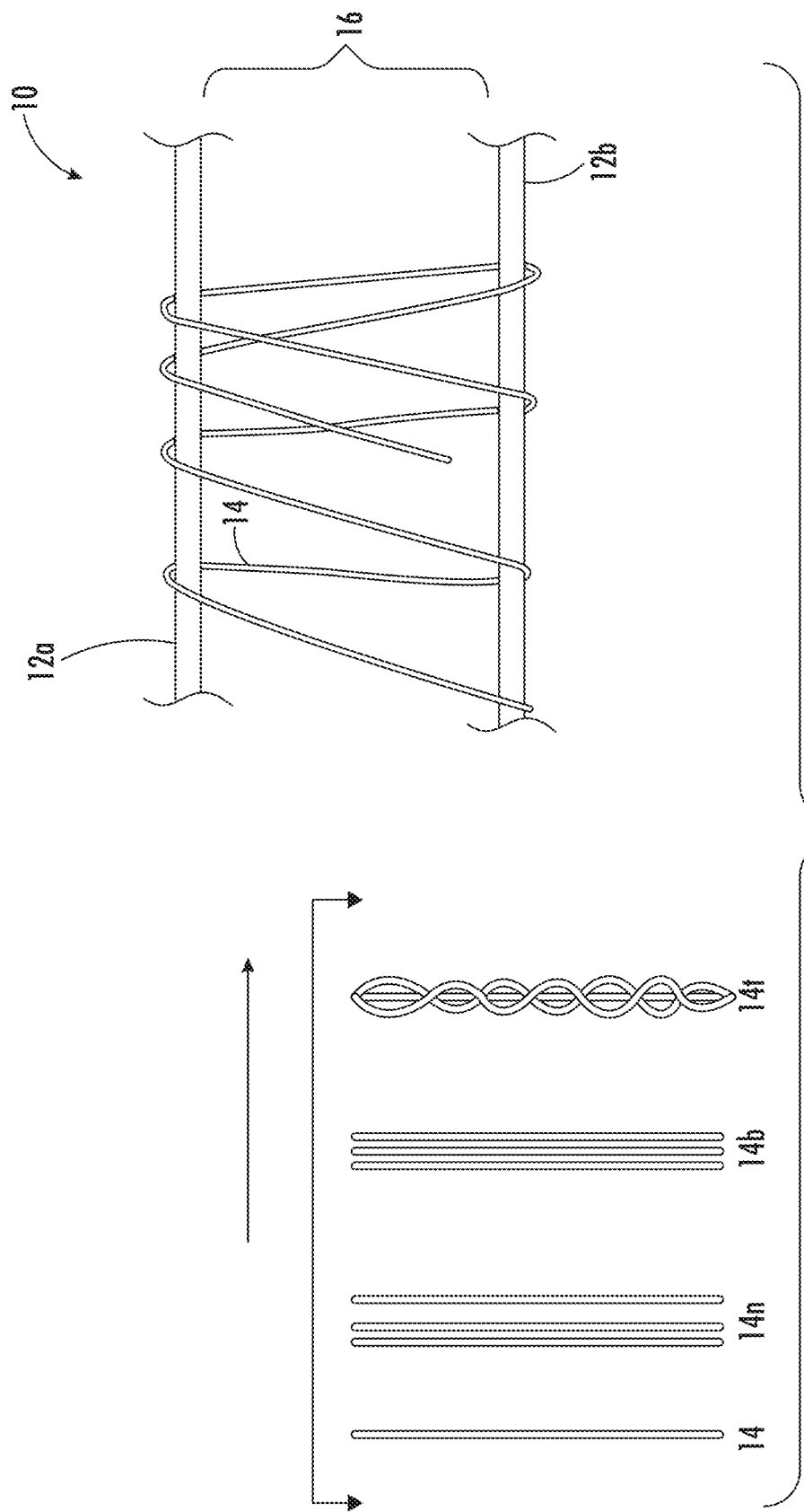

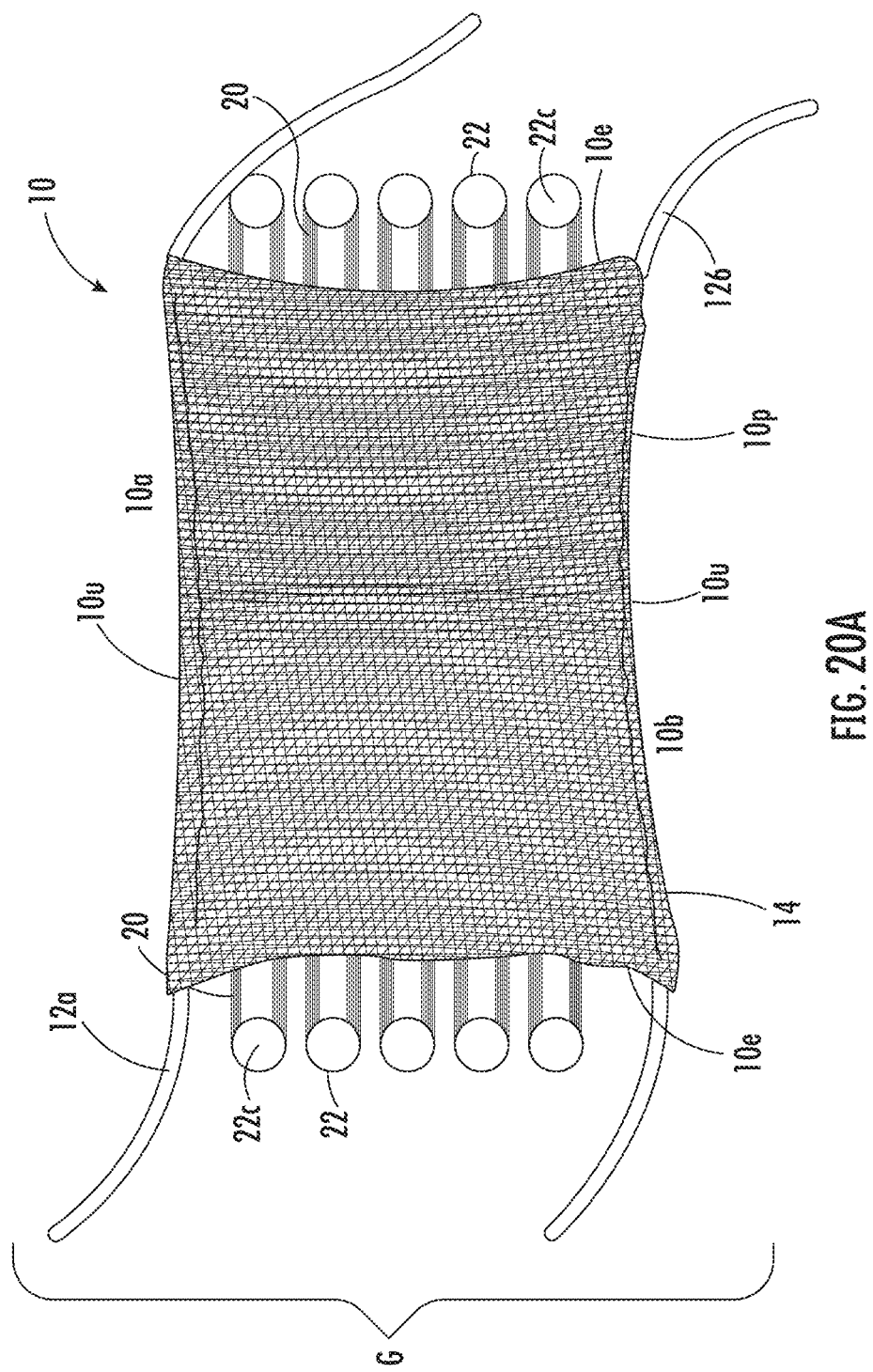

METHODS OF MAKING COLLAGEN FIBER MEDICAL CONSTRUCTS AND RELATED MEDICAL CONSTRUCTS, INCLUDING PATCHES

RELATED APPLICATION(S)

This application claims the benefit of and priority to U.S. Provisional Application Ser. No. 62/672,136 filed May 16, 2018, the contents of which are hereby incorporated by reference as if recited in full herein.

FIELD OF THE INVENTION

The invention relates to biomedical materials and products.

BACKGROUND OF THE INVENTION

Methods and uses of collagen fibers to make various medical constructs are known. See, for example, U.S. Pat. Nos. 8,367,148; 9,125,759; and 9,078,775, and U.S. Patent Publication No. 2015/0283305, the contents of each of which are hereby incorporated by reference in their entirety as if recited in full herein. However, there remains a need for medical constructs capable of providing different medical properties.

SUMMARY OF THE INVENTION

A first aspect of the present invention is directed to a method of manufacturing a medical construct. The method may comprise providing a first support and a second support that are spaced apart from each other with an open medial space extending therebetween, wherein the first and second supports each have a length; winding at least one continuous length collagen fiber across the open medial space, about the first support, and about the second support, optionally wherein the at least one continuous length collagen fiber is wet; repeating winding the at least one continuous length collagen fiber a plurality of times such that the at least one continuous length collagen fiber is wound over at least a portion of the length of each support; and forming a medical construct comprising a plurality of overlying layers of the at least one continuous length collagen fiber based at least in part on the winding.

The method may further include the first support and the second support being substantially parallel to each other. The medical construct may be a planar construct. The first support and the second support may be each flexible biocompatible supports held in tension during the winding of the at least one continuous length collagen fiber. The first support and the second support may be rigid.

The method may further include providing a plurality of spaced apart posts within the open medial space between the first support and the second support, wherein the plurality of spaced apart posts project/extend above and/or below the first support and the second support; and looping the at least one continuous length collagen fiber and/or an at least one continuous length biocompatible fiber and/or yarn about the plurality of posts.

The looping may form a closed-circle loop or an open semi-circular loop corresponding to one or more respective spaced apart posts.

The plurality of spaced apart posts may include a first plurality of posts and a second plurality of posts. The first plurality of posts may be longitudinally spaced apart from the second plurality of posts in relation to the first and second supports. The looping may be carried out to loop the at least one continuous length collagen fiber and/or the at least one continuous length biocompatible fiber and/or yarn back and forth between the first plurality of posts and the second plurality of posts.

The looping may be carried out to form loops of the at least one continuous length collagen fiber and/or the at least one continuous length biocompatible fiber and/or yarn that reside within a perimeter boundary of the medical construct formed by the winding of the continuous length collagen fiber. The looping may be carried out to form loops of the at least one continuous length collagen fiber and/or the at least one continuous length biocompatible fiber and/or yarn that extend outside the perimeter boundary of the medical construct formed by the winding of the continuous length collagen fiber. The winding may be carried out to form overlaying and abutting layers of the at least one continuous length collagen fiber. The method may further comprise applying a polymeric film to the medical construct.

The first and second supports may comprise a biocompatible fiber, yarn or suture that is integrated into the medical construct.

The winding may comprise a winding sequence of winding the at least one continuous length collagen fiber in a range of about 345 degrees to about 360 degrees about the first support; then winding the at least one continuous length collagen fiber across the open medial space between the first support and the second support to the second support; then winding the at least one continuous length collagen fiber in a range of about 345 degrees to about 360 degrees about the second support; then winding the at least one continuous length collagen fiber back across the open medial space to the first support; and repeating the winding sequence a plurality of times over at least a portion of the length of the first support and the second support.

The providing step may further comprise providing a third support having a length, wherein the first, second and third supports are oriented so that each of the first, second and third supports cross the other two supports at a point along the length of each support, and wherein the winding is carried out to wind the at least one continuous length collagen fiber about each of the first, second and third supports. The forming step may further comprise forming a planar triangular medical construct.

Another aspect of the present invention is directed to a method of manufacturing a medical construct. The method may comprise providing a first support and a second support, each support having a length extending in a longitudinal direction, the first support and the second support being laterally spaced apart with an open medial space therebetween; winding at least one biocompatible fiber and/or yarn across the open medial space, about the first support, and about the second support, optionally wherein the at least one biocompatible fiber and/or yarn is wet; repeating winding the at least one biocompatible fiber and/or yarn a plurality of times such that the at least one biocompatible fiber and/or yarn is wound over at least a portion of the length of each support to form a fiber grid; winding at least one continuous length collagen fiber a plurality of times about a length of the fiber grid; and forming a medical construct comprising the fiber grid and a plurality of overlying layers of the at least one continuous length collagen fiber based, at least in part, on the winding.

The winding of the at least one biocompatible fiber and/or yarn across the open medial space provides adjacent may directly contacting layers of the at least one biocompatible fiber and/or yarn between the first support and the second support.

At least a portion of the at least one biocompatible fiber and/or yarn may be arranged parallel to the longitudinal axis of at least one of the first support and the second support. At least a portion of the at least one biocompatible fiber and/or yarn may be arranged perpendicular relative to the longitudinal axis of at least one of the first support and the second support.

The fiber grid may be a first fiber grid and the at least one biocompatible fiber and/or yarn may be a first biocompatible fiber and/or yarn. The method may further comprise winding at least one second biocompatible fiber and/or yarn over and under the first fiber grid to form a second fiber grid. The method may further comprise applying a polymeric film to the fiber grid and/or the medical construct.

A further aspect of the present invention is directed to a method of manufacturing a medical construct. The method may comprise providing a core comprising a plurality of synthetic collagen fibers; wrapping a layer comprising at least one continuous length synthetic collagen fiber a plurality of revolutions around the core, so that the at least one continuous length synthetic collagen fiber has at least one defined pitch and/or fiber angle that is offset to a longitudinal axis of the core, thereby forming the medical construct. The plurality of synthetic collagen fibers may extend substantially parallel along the longitudinal axis of the core.

A further aspect of the present invention is directed to a medical patch. The medical patch may comprise a patch body comprising a perimeter with a first side and an opposing second side, each of the first and second sides having an outer edge portion, wherein each outer edge portion comprises at least one biocompatible fiber, yarn, or suture extending parallel to the first and second sides; and at least one continuous length collagen fiber that extends a plurality of times across the patch body in a mesh pattern having a plurality of overlying layers defining interstitial spaces and at least a portion of the at least one continuous length collagen fiber extends in a range of about 345 degrees to about 360 degrees about an outer surface of the at least one biocompatible fiber, yarn or suture of the outer edge portion of the first and second sides.

The at least one biocompatible fiber, yarn, or suture may have a diameter that is greater than a diameter of the at least one continuous length collagen fiber. The medical patch may further comprise a polymeric film that extends over the interstitial spaces. The polymeric film may cooperate with the at least one continuous length collagen fiber to form an impermeable patch body to thereby prevent fluid leakage through the medical patch when implanted.

The medical patch may further comprise at least one suture anchor aperture in the fiber mesh pattern, wherein the at least one suture anchor aperture may have a size greater than the interstitial spaces to thereby allow a suture to pass therethrough.

The medical patch may further comprise a biocompatible yarn residing within the patch body spaced apart from the outer edge portion of the first and second sides.

The medical patch may further comprise a plurality of loops of the at least one biocompatible yarn or suture extending between and/or outside the outer edge portions of the first and second sides of the patch body. One or more of the plurality of loops may reside within the patch body and define at least one suture anchor aperture. One or more of the plurality of loops may reside outside the patch body and have a closed-circle loop shape.

The patch body may further comprise a third side, the at least one continuous length collagen fiber further extending a plurality of times across the patch body and about the third side of the patch body to form the mesh pattern. The patch body may further comprise an inner layer comprising at least one biocompatible fiber arranged in a fiber grid pattern under the fiber mesh pattern.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 is a schematic illustration of different continuous length collagen fiber configurations that may be used for forming a medical construct according to embodiments of the present invention.

FIG. 20A is a top view image of an example medical patch according to embodiments of the present invention.

DETAILED DESCRIPTION OF THE INVENTION

Figure 1:
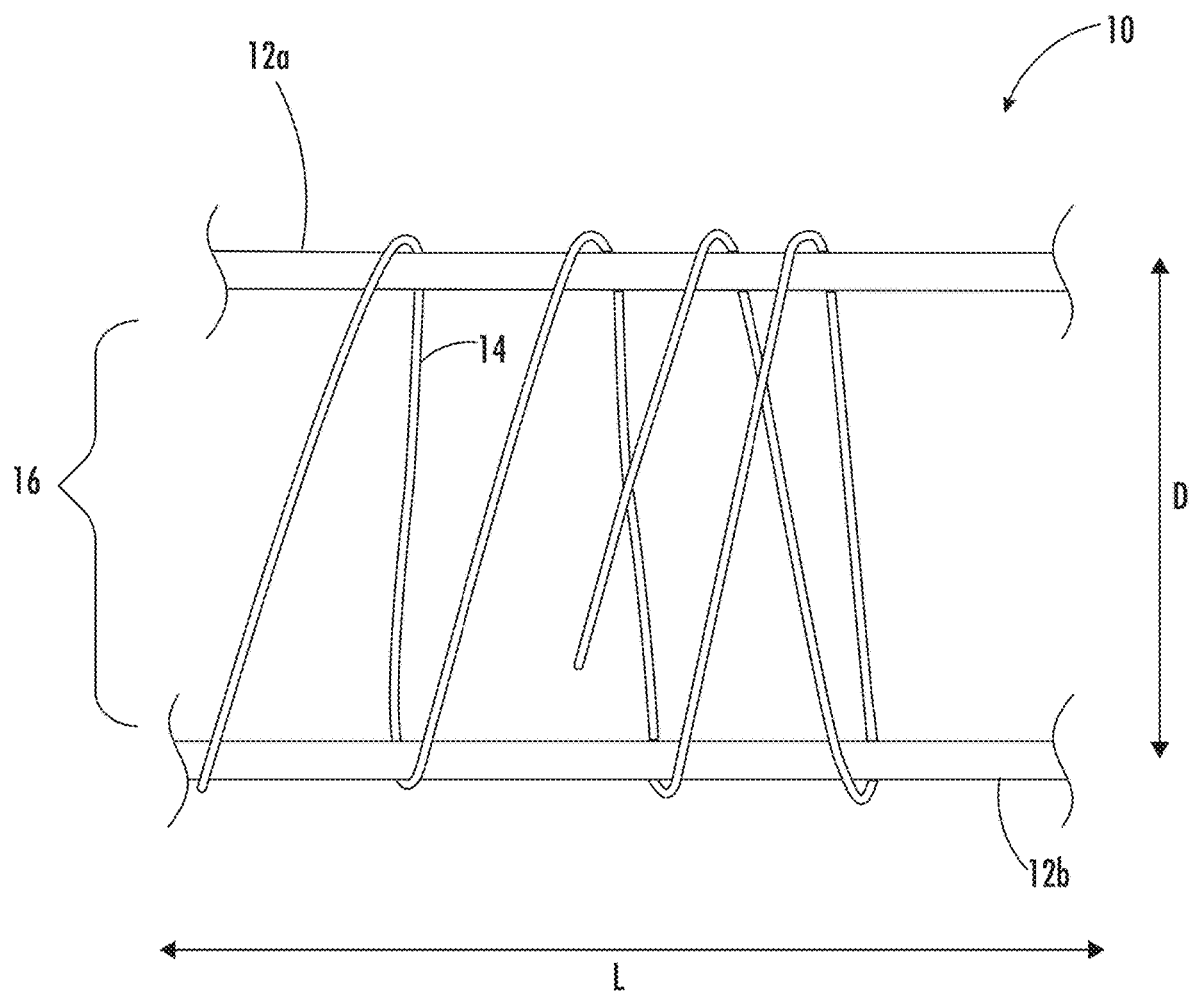
FIG. 1 is a schematic illustration of an example method of forming a medical construct according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention now will be described more fully hereinafter with reference to the accompanying drawings, in which illustrative embodiments of the invention are shown. Like numbers refer to like elements and different embodiments of like elements can be designated using a different number of superscript indicator apostrophes (e.g., 10, 10', 10").

In the figures, certain layers, components or features may be exaggerated for clarity, and broken lines illustrate optional features or operations unless specified otherwise. The terms "FIG." and "Fig." are used interchangeably with the word "Figure" in the application and/or drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

The term "about" when referring to numbers in a range (e.g., from about X to about Y) refers to +/−20% of the noted value. The term "about" may also be used to refer to an element or feature's relationship to another element(s) or feature(s) (e.g., a fiber wound about a support). It will be understood that when an element or feature is referred to in this manner, it can mean around, over, under, and/or across.

It will be understood that when an element is referred to as being "on", "attached" to, "connected" to, "coupled"

with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "implantable" and derivatives thereof means the device can be inserted, embedded, grafted or otherwise acutely or chronically attached or placed in or on a patient. The term "construct" refers to a device and/or material in a final form for use or in a pre-final form.

The term "pitch" means winding the fiber at an angle relative to a first plane normal to the longitudinal axis of a core or support and/or a wound fiber that is at an angle relative to a first plane normal to the longitudinal axis of a core or support.

The word "embedded" and derivatives thereof in reference to a collagen fiber mean that at least a portion of the collagen fiber is held in a polymeric matrix and/or encased by a polymeric material (e.g., a polymeric matrix and/or film).

The term "patch" refers to a piece or segment of biomaterial that can be placed on and/or affixed to a target anatomical structure, typically soft tissue, to treat, protect, repair and/or reinforce a target site. The patch can be any geometric shape but is typically substantially planar and may, in position, conform to the shape of underlying or overlying tissue.

The terms "winding" and "wound" and derivatives thereof mean to wrap about at least two spaced apart objects a plurality of times, typically repeatedly in a defined direction or directions, e.g., to turn in a series of oval, elliptical or similar motions. The winding may define a continuous length collagen fiber having a woven fiber arrangement with a number of revolutions, typically in a regular pattern (but an irregular pattern may also be used) about a length of at least two objects.

Embodiments of the present invention comprise collagen, typically dermal or placental collagen. However, the collagen can be of any form and from any origin. The collagen can be any of the identified collagen genotypes such as, for example, the interstitial fiber forming collagen types I, II and III, as well as any other substantially fiber forming types of collagen, for example collagen VI. The collagen can be acid soluble collagen or pepsin solubilized and/or soluble collagen. The collagen can be from mammalian cells synthesized in vitro. The collagen can be from molecularly engineered constructs and synthesized by bacterial, yeast or any other molecularly manipulated cell type. For example, the collagen can be sea cucumber dermis collagen, bovine, caprine, porcine, ovine, human or other suitable donor mammal collagen, marine animal collagen such as chinoderms, molecularly engineered collagen, or gelatin (e.g., in any suitable form including solid, gel, hydrogels, liquids, or foams). In some embodiments, the collagen may be human collagen, including, but not limited to, human placental collagen. In addition, the collagen can be digested with a protease before, where used, oxidizing and polymerizing steps. The collagen can be in the form of microfibrils, fibrils, natural fibers, and/or synthetic fibers.

In some embodiments, the collagen can be solubilized, dissolved or otherwise transferred into an acid solution, for example, acetic acid (e.g., about 0.01 M to about 1.0 M, typically about 0.5 M), hydrochloric acid (e.g., from about pH 1 to about pH 3, typically about pH 2.0), or any other suitable acid at appropriate concentration (e.g., about pH 1.0 to about pH 3.0, typically about pH 2.0). Dialysis may optionally be used to neutralize a soluble collagen solution. The collagen can also or alternatively be dissolved in a neutral buffered solution either with or without salts, e.g., phosphate buffer at about pH 7.0, or phosphate buffered saline at about pH 7.0. The phosphate buffer can be at any concentration of sodium phosphate from about 0.01 M to 0.5 M, but more typically from about 0.02 M to about 0.1 M. The buffer can also be any buffer, including, but not limited to, for example, sodium acetate, HEPES, or MOPS. The collagen can be present in a solution (e.g., a buffer) in an amount of about 0.1% to about 10%, typically about 0.1% to about 5% (e.g., about 0.1%, 0.2%, 0.3%, 0.4%, 1.0%, 2.0%, 4.0%) by weight per volume of the solution before fibrillogenesis and fiber formation. In a dried collagen fiber, collagen may be present in an amount of about 50% to about 100% (e.g., at least about 75%, 90%, 95% or 100%) before crosslinking (where crosslinking is used).

Collagen "microfibrils," "fibrils," "fibers," and "natural fibers" refer to naturally-occurring structures found in a tendon. Microfibrils are about 3.5 nm to about 50 nm in diameter. Fibrils are about 50 nm to about 50 µm in diameter. Natural fibers are above 50 µm in diameter. A "synthetic fiber" refers to any fiber-like material that has been formed and/or chemically and/or physically created or altered from its naturally-occurring state. For example, an extruded collagen fiber of fibrils formed from a digested tendon is a synthetic collagen fiber but a tendon fiber newly harvested from a mammal is a natural collagen fiber. "Fiber" refers to a single filament. "Yarn" refers to multiple single filaments (i.e., fibers) spun, braided, or twisted together.

In some embodiments, other materials may be used with a collagen fiber to form an elastic construct. For example, non-cytotoxic (and typically non-inflammatory) polymers including thermoplastic materials and/or polymers based on monomers such as acrylates, e.g., polymers which are prepared by copolymerizing two or more of the monomers such as alkyl acrylate monomers (e.g., methyl acrylate, ethyl acrylate, butyl acrylate or octyl acrylate); alkyl methacrylate monomers (e.g., methyl methacrylate or ethyl methacrylate); acrylic acid or methacrylic acid; vinyl cyanide monomers (e.g., acrylonitrile or methacrylonitrile); aromatic vinyl monomers (e.g., styrene or a-methylstyrene); and vinyl halide monomers (e.g., vinyl chloride or vinyl bromide). In addition to the monomers, cross-linking agents such as divinylbenzene, monoethylene glycol dimethacrylate and polyethylene glycol dimethacrylate may be used alone or as a mixture of two or more. In some embodiments, alkyl methacrylate monomers and aromatic vinyl monomers may be used and/or polymerized, with an alkyl acrylate monomer and an alkyl methacrylate monomer. Combinations of an alkyl acrylate monomer and an aromatic vinyl monomer for a biocompatible thermoplastic material may be useful, including, but not limited to, a combination of butyl acrylate and methyl methacrylate and a combination of butyl acrylate and styrene.

The synthetic collagen fibers and/or polymeric and/or thermoplastic materials can include other non-collagenous components or biocompatible materials, such as therapeutic agents. The term "therapeutic agent" means biologically active agents, drugs and/or compounds for generating a clinical therapeutic effect. Examples of such agents or drugs include, but are not limited to, particulates, hydroxyapatite and other mineral phases, and/or drugs that facilitate tissue growth, inhibit inflammation, treat infections, reduce pain, thin blood, inhibit coagulation, blockage, plaque build-up or provide other desired therapies or effects, including, in some embodiments, heparin and/or growth hormones. See, e.g., U.S. Pat. No. 6,821,530, incorporated herein by reference above. For example, the fibers and/or constructs formed from the same, can include carbon nano-tubes, zinc nano-wires, nano-crystalline diamond, or other nano-scale particulates, and larger crystalline and non-crystalline particulates such as calcium phosphate, calcium sulfate, apatite minerals. For example, the fibers and/or constructs may contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, decorin, fibromodulin, COMP, elastin, and fibrillin. In some embodiments, the fibers and/or constructs can contain cells, such as, but not limited to, engineered cells, stem cells, and the like. Combinations of the above or other materials can be embedded, coated and/or otherwise directly or indirectly attached to a collagen fiber(s) (such as in a liquid polymeric material used to apply a film) and/or construct formed of the same.

A collagen fiber of the present invention can be formed from a collagen gel that includes collagen fiber, fibrils and/or microfibrils, typically dermal or placental collagen, that has been acid or pepsin solubilized (e.g., soluble collagen) and processed to maintain the collagen in its molecular form. The collagen concentration of the soluble collagen and/or resulting soluble collagen gel can be about 0.1% to about 4% weight per volume. The soluble collagen gel may be formed to be in a cylindrical shape of a defined length and diameter, typically with a diameter of between about 0.1 cm to 1 cm, and a length of about 5 cm to about 100 m, more typically a length of about 10 m to about 50 m, which is subsequently dried to form a collagen fiber.

The collagen fiber and/or collagen gel can be produced in batch or continuous-type systems, including wet gel collagen extrusion systems, which produce cylindrical lengths of gel that can be allowed to substantially dry (actively or passively) to obtain a suitable length of fiber. Examples of some collagen fiber production processes that can generate soluble collagen in suitable lengths are described in U.S. Pat. No. 6,565,960 and pending U.S. Patent Application Publication No. 2008/0188933A1, the contents of which are hereby incorporated by reference.

The collagen fiber(s) can be spooled (e.g., held wound on a spool) for supplying to an automated or semi-automated winder to form a medical construct and/or biomaterial. The spooled fiber(s) can be in a dry state or may be in a hydrated or partially hydrated state. The collagen fiber(s) may be formed with a relatively thin diameter, such as, for example, from about 0.05 mm to about 0.2 mm (average) (dry or wet), such as about 0.08 mm dry diameter (average) and/or about a 0.13 mm wet diameter (average). At least one collagen fiber on the spool for the winding can be formed as a single continuous length of about 1 m to about 100 m or may be formed with multiple fibers joined end-to-end or a single length to form a desired length for the winding.

A component of a medical construct of the present invention (e.g., a collagen fiber) and/or a medical construct of the present invention may be dry or hydrated (e.g., partially or fully hydrated). The term "dry" as used herein means the component and/or medical construct has a water content of less than about 5% by weight of the respective component and/or medical construct. The term "partially hydrated" as used herein means that the component and/or medical construct has a water content that is less than about 100% of the water content at full hydration. In some embodiments, full hydration is measured ex vivo after 24 hours in a saline bath at ambient conditions and compared to the component and/or medical construct at a dry weight. In some embodiments, the component and/or medical construct may have a water content of less than about 25% by weight of the respective component and/or medical construct, such as less than about 15% by weight of the respective component and/or medical construct.

It is noted that the present invention contemplates using one or more thermoplastic material(s) to provide a desired elasticity and the thermoplastic material(s) can be non-cytotoxic (and typically also anti-inflammatory). For discussion purposes, the specification primarily describes acrylates but the invention is not intended to be limited to acrylates as the thermoplastic material. The use of acrylates is for exemplary purposes.

In some embodiments of the present invention, medical constructs can be made from at least one collagen fiber and a non-cytotoxic polymeric material such as, e.g., polyacrylate emulsions and/or other thermoplastic materials, and the collagen fiber(s) can be either cross-linked or uncrosslinked. The polymeric material can be applied in a liquid state to the collagen fiber. In some embodiments, the liquid polymeric material can be a microemulsion. The polymeric material can further include one or more additives including, but not limited to, surfactants, antioxidants, solvents, polymerization inhibitors, chain transfer agents, fillers, thickening agents, flow agents, polymerization initiators and accelerators, lubricants, air release agents, wetting agents, UV stabilizers, compatibilizers, fire retardants, urethane reaction catalysts, moisture scavengers, shrink-reducing additives, and/or one or more therapeutic agent(s).

The polyacrylate emulsion can be homo and/or co-polymer based and may include small molecular weight constituents and/or compounds (typically water soluble). The medical constructs can have multiple applications in the medical field as a biomaterial, such as for artificial tissue or other application including wound care and treatment. The resulting medical constructs can be an elastomeric material with structural integrity and/or sufficient strength for its target use. The medical constructs can have a controlled elasticity suitable for elastic tissue repairs, including, but not limited to, elastic vessel replacements, elastic skin or wound repairs or replacements, lung tissue repairs or reinforcements, and cardiac tissue repairs or reinforcements. Some embodiments of the invention provide medical constructs that have a "memory shape" structure so that after elastically deforming, the material substantially returns to an original shape or configuration without damaging the structural integrity and functionality of the material. The medical constructs can be configured to cycle through a number of stress/relaxation cycles sufficient to provide the desired therapy and corresponding to the target use. The medical constructs can substantially simulate or correspond to the mechanical properties (elasticity) of natural "healthy" or normal tissue elasticity and structure.

The medical constructs can be provided and/or formed by any suitable process or method into various arrays including but not limited to, braids, weaves, twists, and the like, with various patterns of fiber(s) in various orientations and fiber densities (dense to sparse and tight to loose geometries) to meet the desired mechanical properties for the target use.

The term "film" as used herein refers to a thin layer of a coating material. A film is typically present in a thickness that is from about 5 μm to about 5 mm. The film may embed the collagen fiber(s) so as define a combined biocomposite material with a thickness of about 0.5 mm to about 6 mm, typically about 1 mm to about 5 mm (average, dry). The film may be permeable and/or flexible. In some embodiments, the film may be permeable to only small ions or low molecular weight (<150 g/mol) compounds. The film may be optically transmissive, e.g., translucent or transparent, or may be opaque. Several layers of the same or different polymeric material(s) (e.g., one or more polyacrylate emulsions of the same or different formulations) can be applied to generate the desired coating thickness or coverage. The color or transmissive characteristics of the film may change when hydrated. The film can infuse into, permeate, migrate and/or embed a collagen fiber to form a collagen fiber laminate and/or to encase the collagen fiber. A coating can form a film that may prevent swelling and/or resulting deformation of the device upon hydration. The coating and/or film may provide a smooth (and typically a substantially constant diameter) dry surface over or under the fiber(s) and extend over the interstitial space of the fiber(s) to close the outer and/or inner surface of the construct. For example, the coating and/or film can form a non-cytotoxic thermoplastic material, e.g., a polyacrylate film, which embeds the fiber(s) and extends as a solid film over interstitial spaces of a fiber mesh. The fluid polymeric material can help the fiber(s) retain its wound shape (e.g., inhibit unraveling) during and/or after winding. The film and/or coating can give the construct reversible elasticity and sufficient mechanical properties such as modulus of elasticity and/or structural strength.

Referring now to the figures, FIG. 1 illustrates an example method of forming a medical construct 10 according to some embodiments of the present invention. As seen in FIG. 1, a first support 12a and second support 12b are provided. The first and second supports 12a, 12b are spaced apart from each other a distance (D) with an open medial space 16 extending laterally between the two supports 12a, 12b. The medical construct 10 can be formed by winding at least one continuous length collagen fiber 14 about the first and second supports 12a, 12b.

The continuous length collagen fiber 14 may be wound a plurality of times across the open medial space 16 and about the first support 12a and second support 12b. The winding may be done over at least a portion of the length (L) of each support 12a, 12b. The length (L) of the supports 12a, 12b can vary depending on the final use of the medical construct 10. Typically, the supports 12a, 12b can have a length (L) of about 2.5 cm to about 30.5 cm.

By way of example, the continuous length collagen fiber 14 is wound across the open medial space 16 and about the first support 12a. The continuous length collagen fiber 14 is next wound back across the open medial space 16 and about the second support 12b. The winding of the continuous length collagen fiber 14 is repeated across the open medial space 16 and about the first support 12a and the second support 12b a plurality of times forming a medical construct 10 comprising a plurality of overlying layers $13n$ of the continuous length collagen fiber 14 (see, e.g., FIG. 3B). In some embodiments, the continuous length collagen fiber 14 may be wet (i.e., fully hydrated or partially hydrated) when being wound across the open medial space 16 and about the first and second supports 12a, 12b.

Typically, the continuous length collagen fiber 14 has a length of about 1 m to about 100 m. In some embodiments, a plurality of continuous length collagen fibers 14 may be wound about the first and second supports 12a, 12b to form the medical construct 10 (FIG. 2). In some embodiments, a single continuous length collagen fiber 14 or a single collagen fiber bundle 14b, 14t can be wound about the first and second supports 12a, 12b to form the medical construct 10.

FIG. 2 illustrates different continuous length collagen fiber 14 configurations that may be used for the winding operation/method to form the medical construct 10. Examples of collagen fiber configurations include, but are not limited to, a single continuous length collagen fiber 14, a plurality of discrete continuous length collagen fibers $14n$ (typically n=2 to 100) that can be concurrently or serially wound about the first and second supports 12a, 12b, a continuous length collagen fiber bundle 14b, and a twisted, woven or braided continuous length collagen fiber bundle 14t. For the continuous length collagen fiber bundles 14b, 14t, two or more continuous length collagen fibers 14 can be grouped together to form the continuous length collagen fiber bundle 14b, 14t. The continuous length collagen fiber bundle 14b, 14t may be wound about the first and second supports 12a, 12b similar to a single continuous length collagen fiber 14. In some embodiments, one or more continuous length collagen fiber bundles 14b, 14t may be used to form a medical construct 10. Combinations of the different collagen fiber configurations may also be used to for some medical constructs 10, such as, for example, a twisted continuous length collagen fiber 14t can be co-wound with a single continuous length collagen fiber 14, and/or a single continuous length collagen fiber 14 may be used to form one layer and a twisted continuous length collagen fiber 14t may be used to form a different layer, and the like.

Figure 3A:
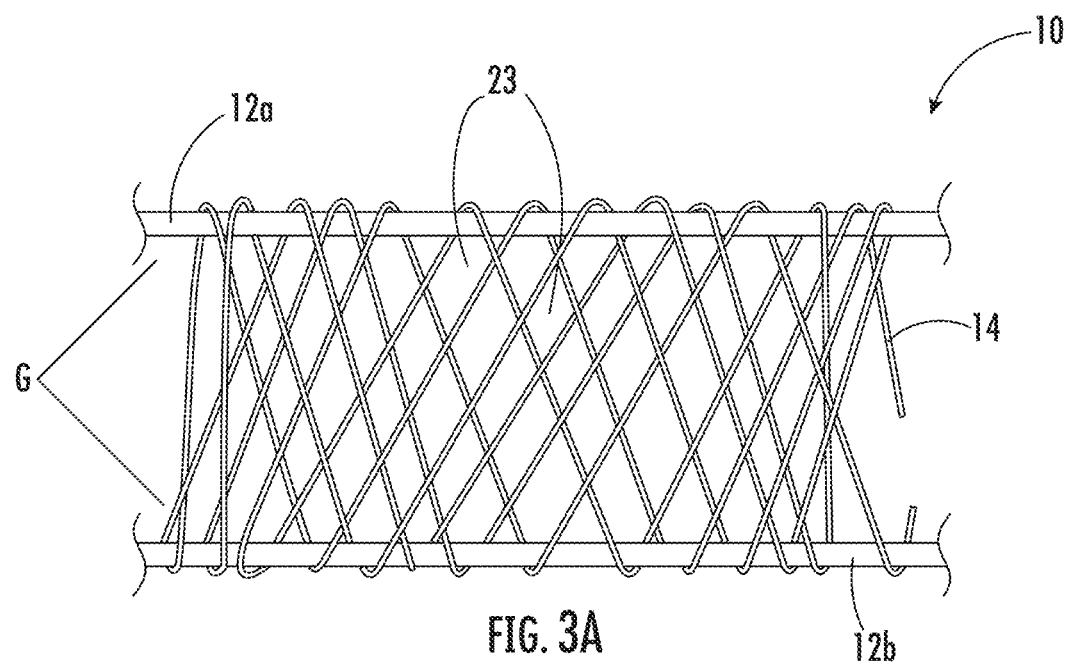
FIG. 3A is a top view schematic illustration showing the example method illustrated in FIG. 1.
Figure 3B:
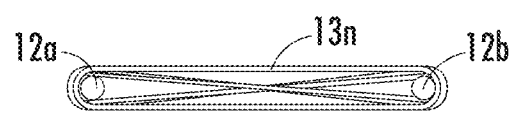
FIG. 3B is an end view schematic illustration showing the example method illustrated in FIG. 3A.

Referring to FIGS. 3A and 3B, the winding of the continuous length collagen fiber 14 can create a plurality of overlying layers $13n$ (typically, n=2 to 100) (FIG. 3B). The overlying layers $13n$ of continuous length collagen fiber 14 may form a mesh pattern or fiber grid (G). As used herein, "fiber grid" generally refers to when fiber(s) and/or yarn(s) cross over and/or under the same or other fiber(s) and/or yarn(s). The plurality of overlying layers $13n$ may define interstitial spaces 23 in the fiber grid (G). The forming of the medical construct 10 may be based, at least in part, on the winding of the continuous length collagen fiber 14.

Figure 4:
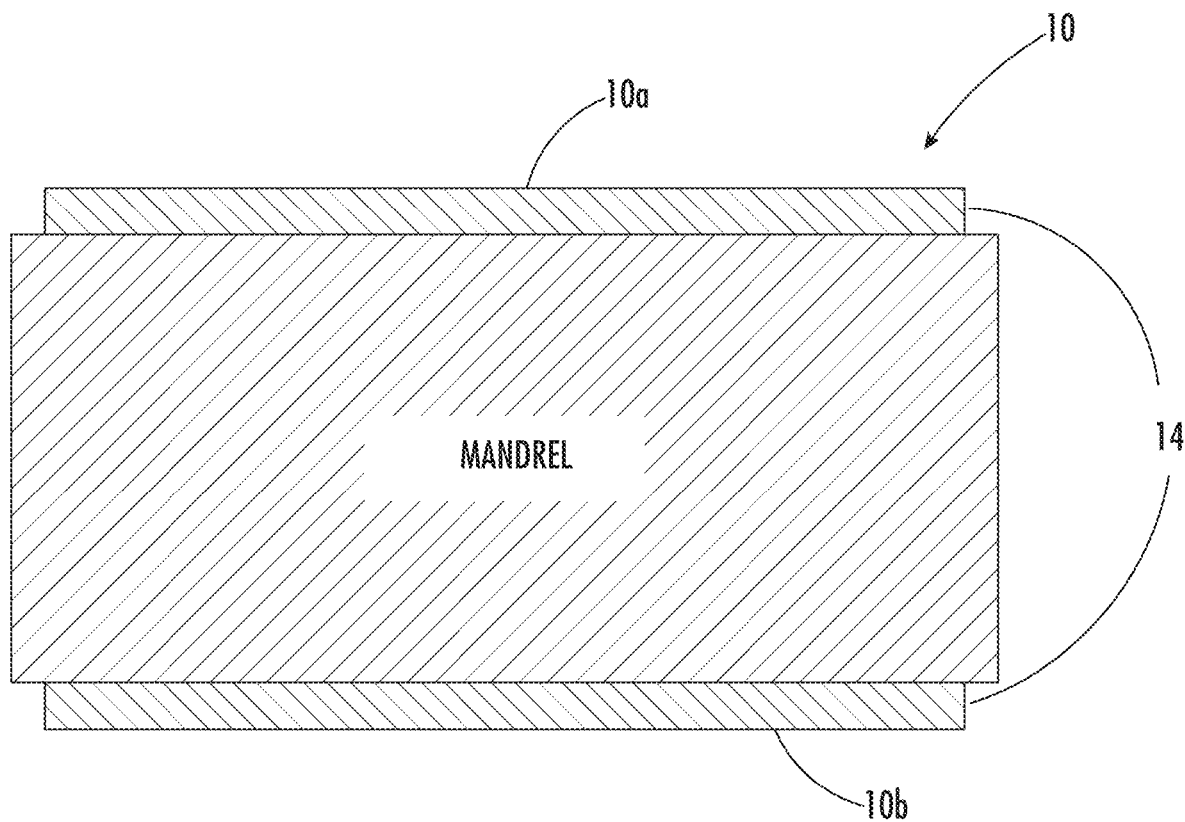
FIG. 4 is a schematic cross-section (in an axial direction) illustration showing a medical construct on a prior art solid mandrel.

Winding the continuous length collagen fiber 14 across an open medial space 16 (opposed to winding about a single, solid mandrel) can form "two sides" of the medical construct 10 as an integrated collagen fiber phase that can result in a solid construct. For example, when winding a wet continuous length collagen fiber 14 across the open medial space 16, the continuous length collagen fiber 14 may come in contact with itself or another continuous length collagen fiber 14 and may anneal, bind, and/or stick together to form an integrated collagen fiber phase. In contrast, as shown in FIG. 4, use of a solid mandrel where the two sides 10a, 10b of the medical construct 10 are separated by the mandrel during manufacturing (i.e., with no open medial space), results in incongruity between the "two sides," or lumen. See also, e.g., U.S. Pat. Nos. 8,367,148 and 9,078,775, the contents of which are hereby incorporated by reference as if recited in full herein. A medical construct 10 of the present invention can have improved mechanical properties over prior medical constructs manufactured using a single, solid mandrel. For example, a medical construct of the present invention may have greater tensile strength compared to prior constructs.

The continuous length collagen fiber 14 can be wound about the first and second supports 12a, 12b using various fiber angles (e.g., pitch angles), such as angles from about 1 degree and about 90 degrees, typically from about 5 degrees and about 60 degrees, such as, for example, 5, 10, 15, 20, 25, 30, 35, 40, 45, 50, 54 and 55 degrees, or other odd or even numbers between 5-70. Where medical constructs 10 having multiple overlying layers 13n of the at least one continuous length collagen fiber 14 are used, one layer may have a first pitch and another layer may have a different pitch. The medical constructs 10 of the present invention may be formed with winding angles of about 5 degrees to about 30 degrees.

In some embodiments, the first support 12a and second support 12b are substantially parallel to each other (e.g., FIG. 1). However, in some embodiments, the first support 12a and second support 12b may be arranged at an angle offset to each other (i.e., if extended, the supports 12a, 12b would cross at some point) (e.g., FIG. 11).

In some embodiments, the first support 12a and second support 12b are flexible biocompatible supports 12a, 12b and may be integrated into the medical construct 10 to form part of the medical construct 10. "Biocompatible" as used herein means compatible with living tissue and/or a living system by not being toxic, injurious, and/or not causing an immunological rejection. The flexible biocompatible supports 12a, 12b are also non-cytotoxic (i.e., non-toxic to cells). In some embodiments, the medical construct 10 can be configured to provide a desired half-life or other suitable life for its intended function (i.e., it may be biodegradable or dissolvable).

Figure 5:
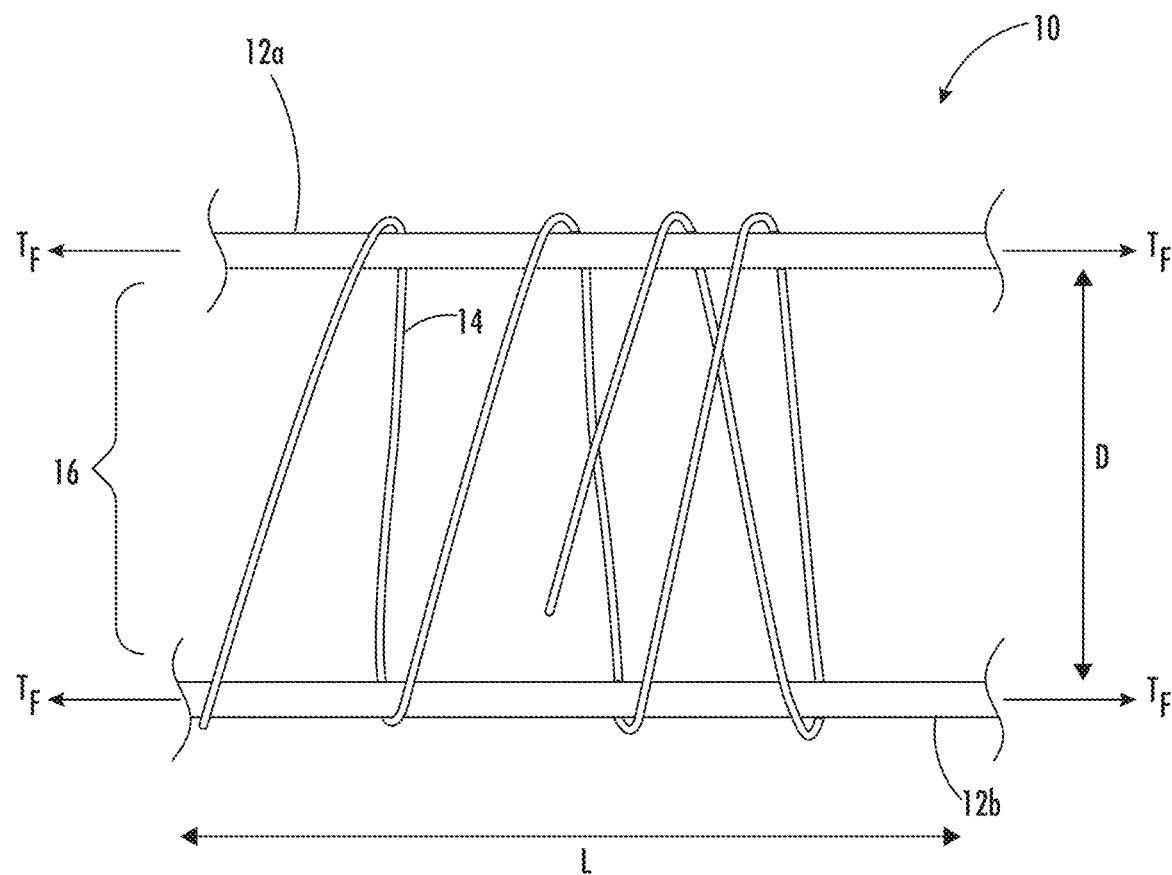
FIG. 5 is a schematic illustration showing an example method of forming a medical construct according to embodiments of the present invention.

Referring now to FIG. 5, in some embodiments, the flexible biocompatible supports 12a, 12b can be held in tension $T_F$ while the at least one continuous length collagen fiber 14 is wound about the flexible biocompatible supports 12a, 12b. The tension $T_F$ should be tight enough to support a continuous length collagen fiber 14 being wound about the flexible biocompatible supports 12a, 12b. The flexible biocompatible supports 12a, 12b may be a biocompatible fiber, yarn, suture or the like. The amount of tension $T_F$ needed can vary depending on the type of biocompatible fiber, yarn or suture being used for the flexible biocompatible supports 12a, 12b.

The winding of the at least one continuous length collagen fiber 14 about the supports 12a, 12b can result in a medical construct 10 with uncut outer edges 10u (see, e.g., FIGS. 19A-19F, FIGS. 20A-20B, and FIGS. 21A-21B). Having a medical construct 10 with uncut outer edges 10u eliminates fraying which can help improve the properties of the medical construct 10, such as, e.g., tensile strength.

Referring to FIGS. 6A-6D, in some embodiments, the supports 12a, 12b may be rigid. As used herein, "rigid" means the supports 12a, 12b are unable to bend or be forced out of shape, i.e., not flexible. In some embodiments, the supports 12a, 12b can be configured to facilitate removal of the medical construct 10 from the supports 12a, 12b. For example, the supports 12a, 12b can include a lubricious and/or smooth surface or an embossed surface with a lower surface contact area, typically a polymer material. In some embodiments, the supports 12a, 12b may comprise Teflon® or other suitable low friction and/or anti-stick material. In some embodiments, the medical construct 10 can be cut in a lengthwise (e.g., longitudinal) direction and taken off the supports 12a, 12b.

Figure 6A:
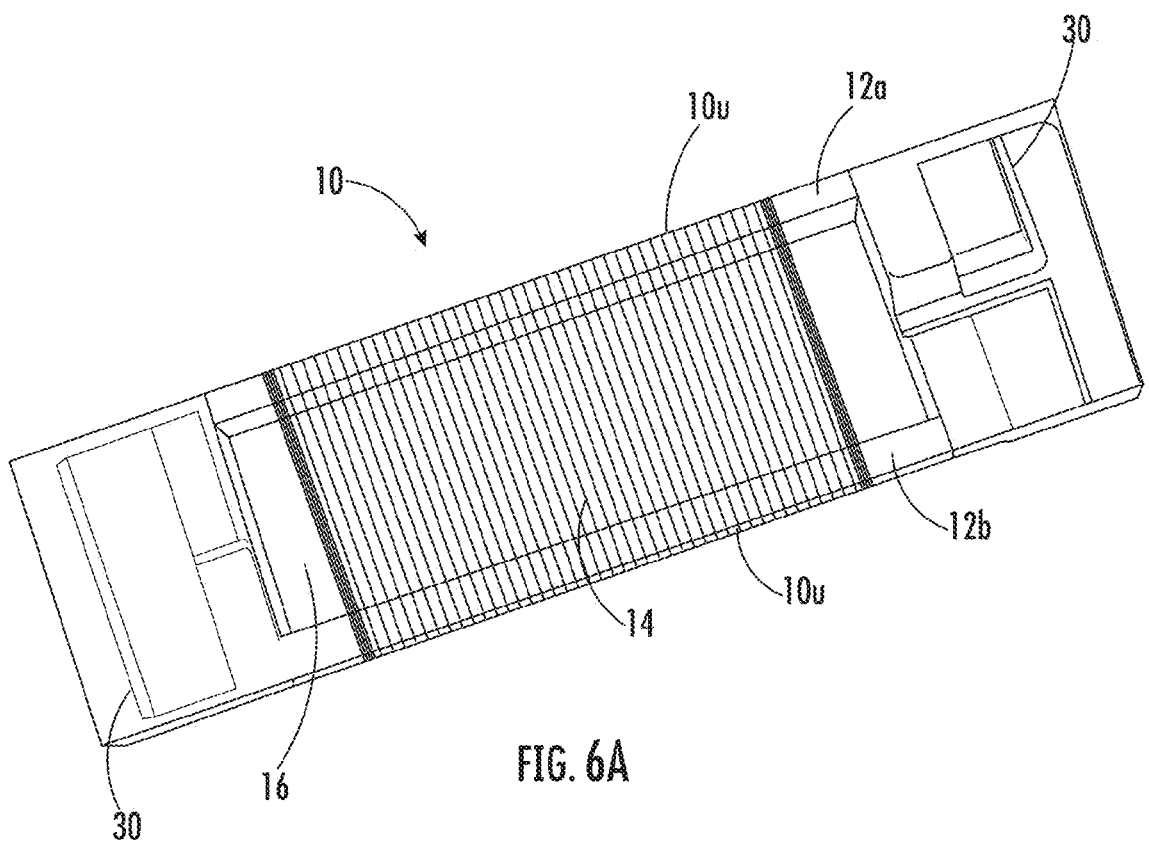
FIG. 6A is a schematic illustration showing an example method of forming a medical construct according to embodiments of the present invention.

In some embodiments, the supports 12a, 12b can be slidably detached from the wound medical construct 10 without being required to cut the edges of the medical construct 10. In some embodiments, the supports 12a, 12b can be held in place by support members 20 as the continuous length collagen fiber 14 is wound about the supports 12a, 12b (FIG. 6A). The support members 30 can be removed from the supports 12a, 12b which can allow the medical construct 10 to be removed from (slid off) the supports 12a, 12b without cutting the outer edges 10u of the medical construct 10.

Figure 6B:
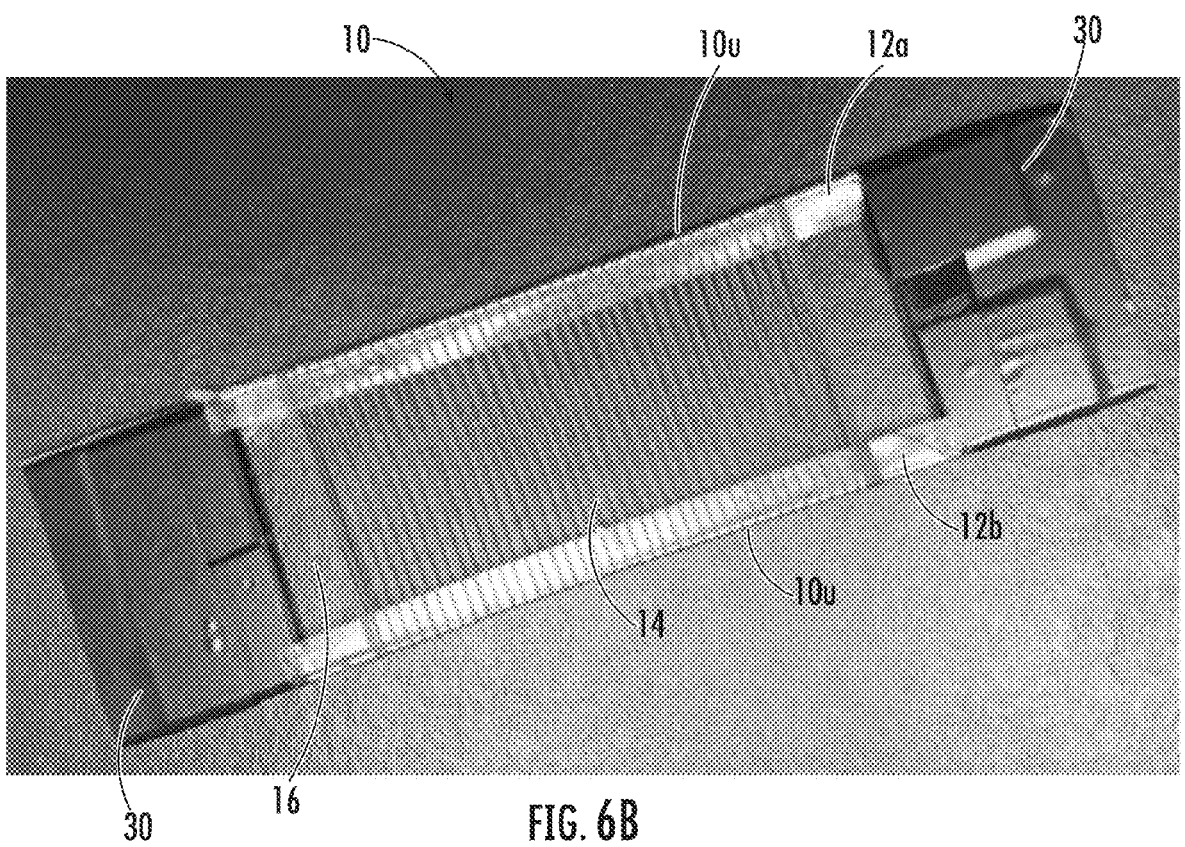
FIG. 6B is a photograph of the example method of forming a medical construct shown in FIG. 6A.
Figure 6C:
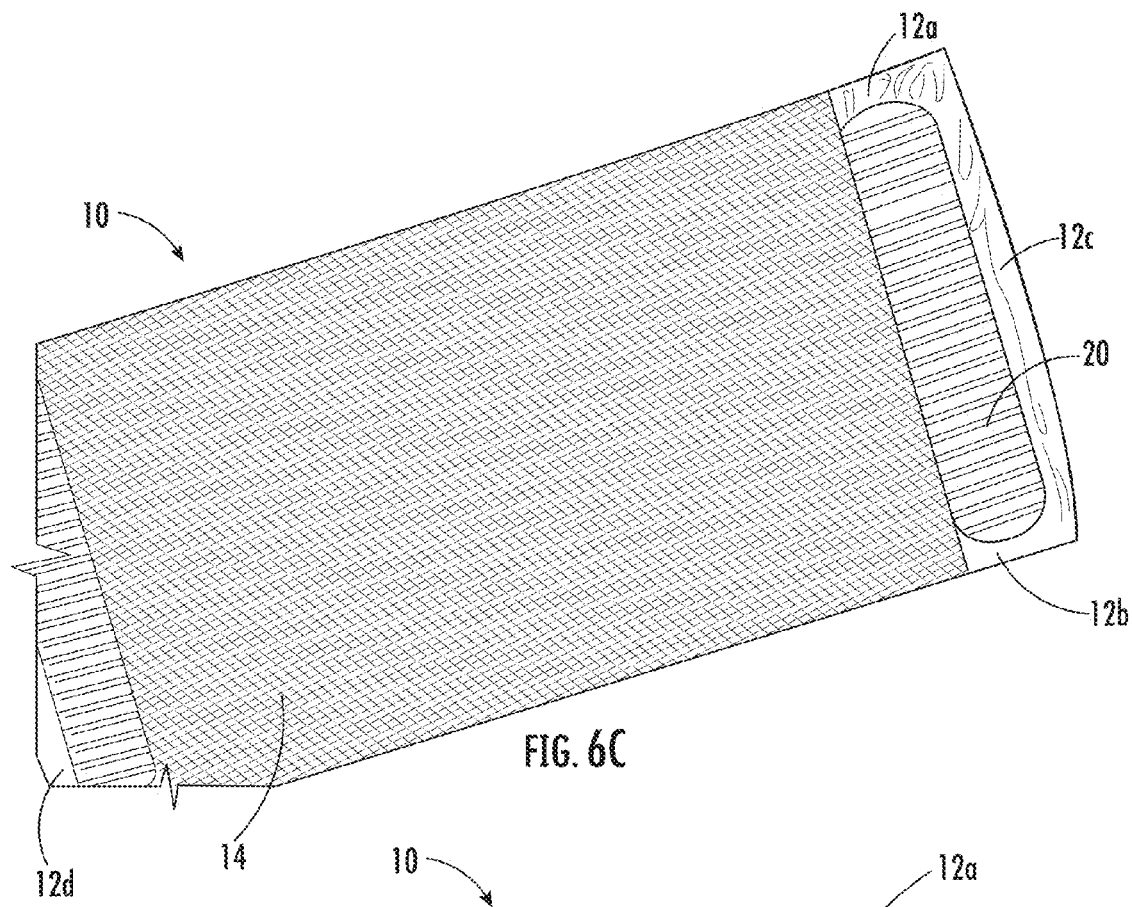
FIG. 6C is a schematic illustration showing an example method of forming a medical construct according to embodiments of the present invention.
Figure 6D:
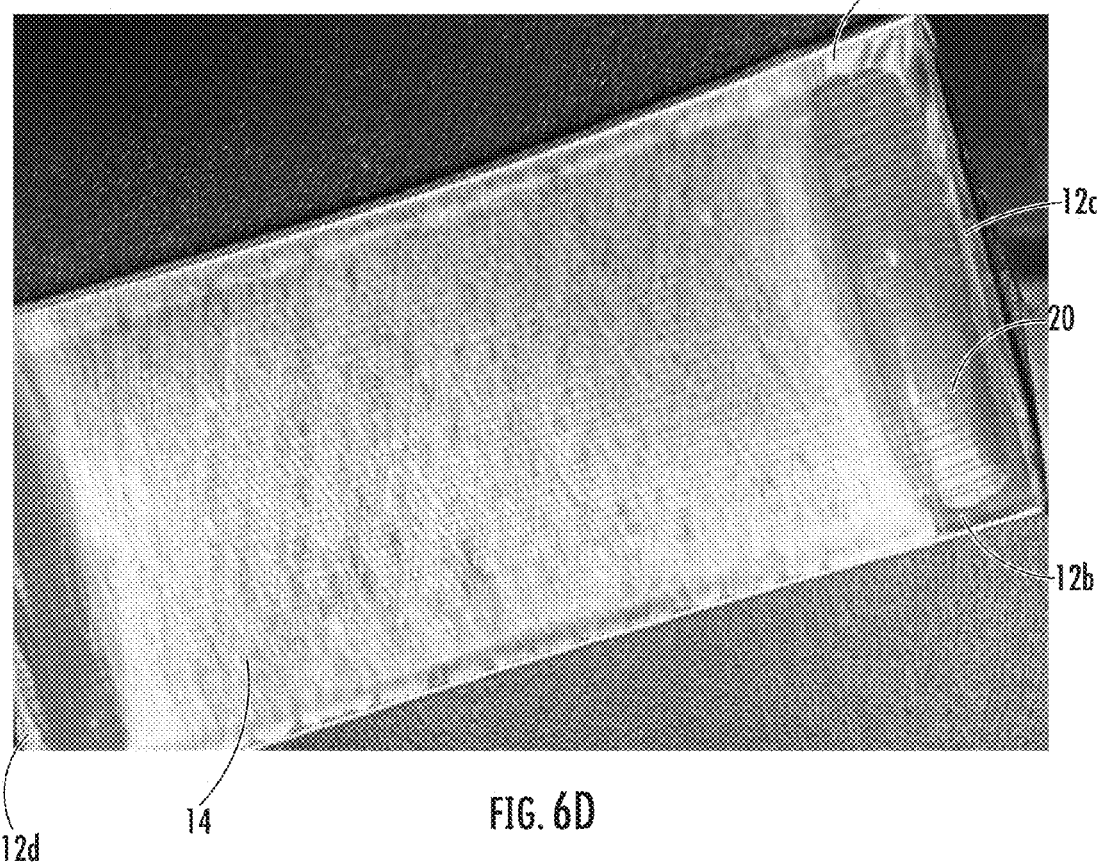
FIG. 6D is a photograph of the example method of forming a medical construct shown in FIG. 6C.

As shown in FIG. 6B, in some embodiments, additional third and/or fourth supports 12c, 12d may be used to form the medical construct 10. In some embodiments, a biocompatible fiber and/or yarn 20 (or continuous length collagen fiber 14) can be wound about supports 12c, 12d. A second continuous length collagen fiber 14 can then be wound about supports 12a, 12b thereby incorporating the biocompatible fiber and/or yarn 20 (or different continuous length collagen fiber 14) into the medical construct 10. In some embodiments, the different continuous length collagen fiber 14 may form an integrated collagen fiber phase. Removal of the medical construct 10 from the supports 12a, 12b, 12c, 12d may require at least one of the edges of the medical construct 10 to be cut.

Figure 7A:
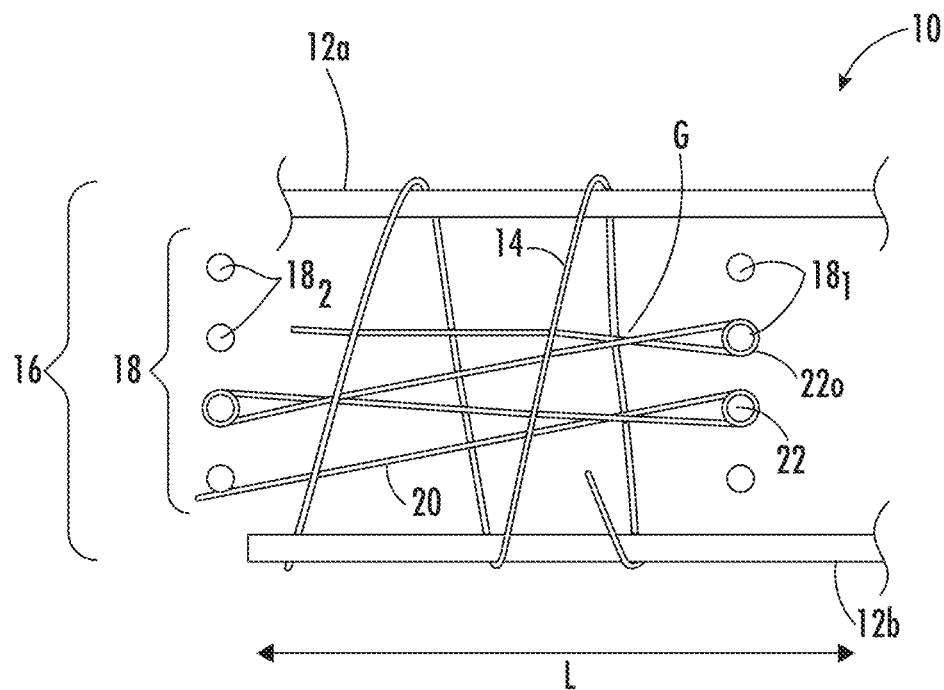
FIG. 7A is a top view schematic illustration showing an example method of forming a medical construct according to embodiments of the present invention.
Figure 7B:
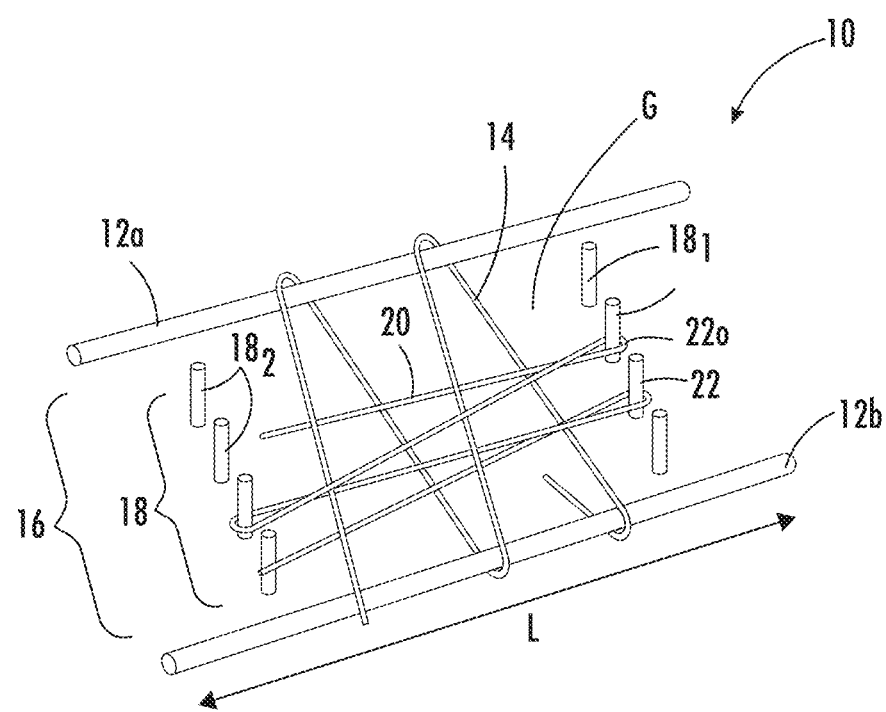
FIG. 7B is a top side perspective view schematic illustration of the example method illustrated in FIG. 7A.

Referring now to FIGS. 7A and 7B, in some embodiments, a plurality of spaced apart posts 18 may be provided within the open medial space 16 extending between the first support 12a and second support 12b. The plurality of spaced apart posts 18 can project/extend above and/or below the first and second supports 12a, 12b. In some embodiments, the continuous length collagen fiber 14 and/or at least one biocompatible fiber 20 (which, in some embodiments, may be a different continuous length collagen fiber 14) may be looped about the plurality of spaced apart posts 18 forming loops 22. In some embodiments, the at least one biocompatible fiber 20 is a yarn. In some embodiments, a plurality of biocompatible fibers and/or yarns 20 (or different continuous length collagen fiber(s) 14) may be wound about the plurality of spaced apart posts 18. This looping of the biocompatible fiber and/or yarn 20 about the plurality of spaced apart posts 18 can be perpendicular to and/or offset to the winding of the continuous length collagen fiber 14 about the first and second supports 12a, 12b and can form the fiber grid (G).

In some embodiments, the plurality of spaced apart posts 18 includes a first plurality of posts $18_1$ that is spaced apart from a second plurality of posts $18_2$. The first and second pluralities of posts $18_1$, $18_2$ may be longitudinally spaced apart. In some embodiments, the looping of the continuous length collagen fiber 14 and/or biocompatible fiber and/or yarn 20 may be carried out to loop the continuous length collagen fiber 14 and/or biocompatible fiber and/or yarn 20 back and forth between the first and second pluralities of posts 18₁, 18₂ to form loops 22 adjacent to each outer edge 10e of the medical construct 10 (e.g., FIG. 19C).

In some embodiments, the continuous length collagen fiber 14 may be wound across the open medial space 16 and about the first support 12a and second support 12b a plurality of times over at least a portion of the length (L) of each support 12a, 12b. The continuous length collagen fiber 14 may also be wound across the biocompatible fiber and/or yarn 20 that is looped about the plurality of spaced apart posts 18 residing within the open medial space 16. The biocompatible fiber and/or yarn 20 can be integrated into the medical construct 10 which may improve the mechanical properties of the medical construct 10, such as, e.g., increasing the tensile strength.

Also shown in FIGS. 7A and 7B, in some embodiments, the posts 18 can reside within the open space 16 extending between the first support 12a and second support 12b. In some embodiments, the posts 18 can be spaced laterally apart and within the length (L) of the supports 12a, 12b, such that the posts 18 reside within a perimeter boundary (10e, 10u) of the medical construct 10 to be formed (see, e.g., FIGS. 19A-19F).

Figure 8A:
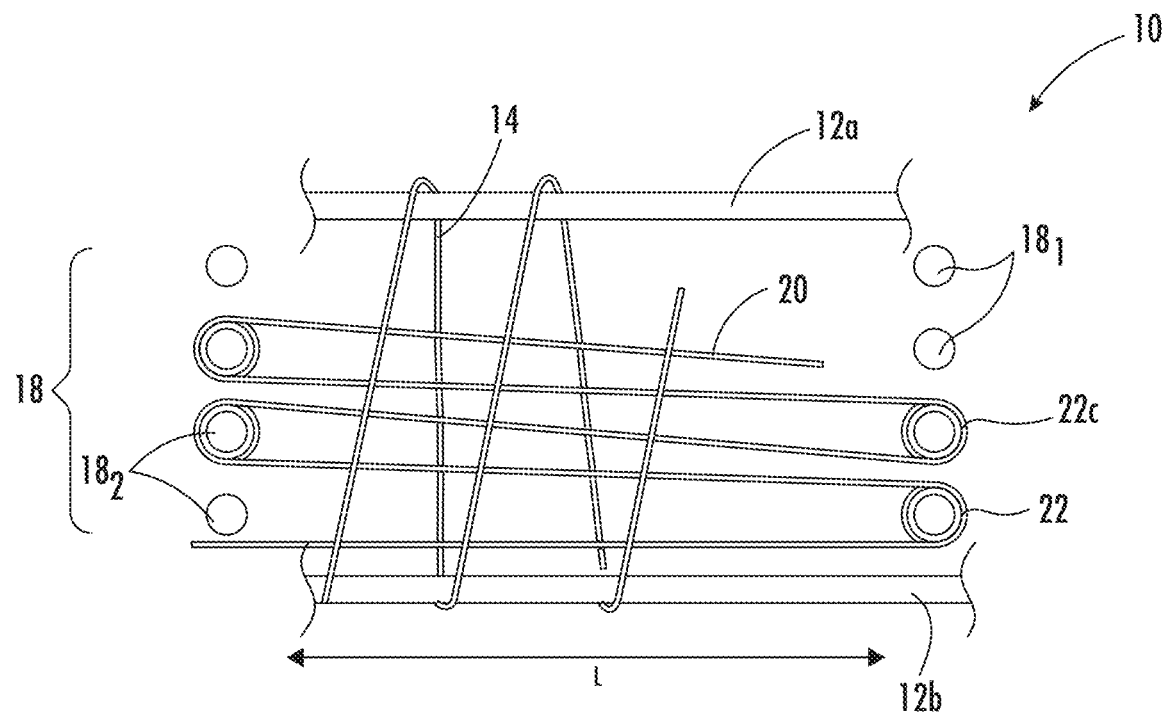
FIG. 8A is a top view schematic illustration showing an example method of forming a medical construct according to embodiments of the present invention.
Figure 8B:
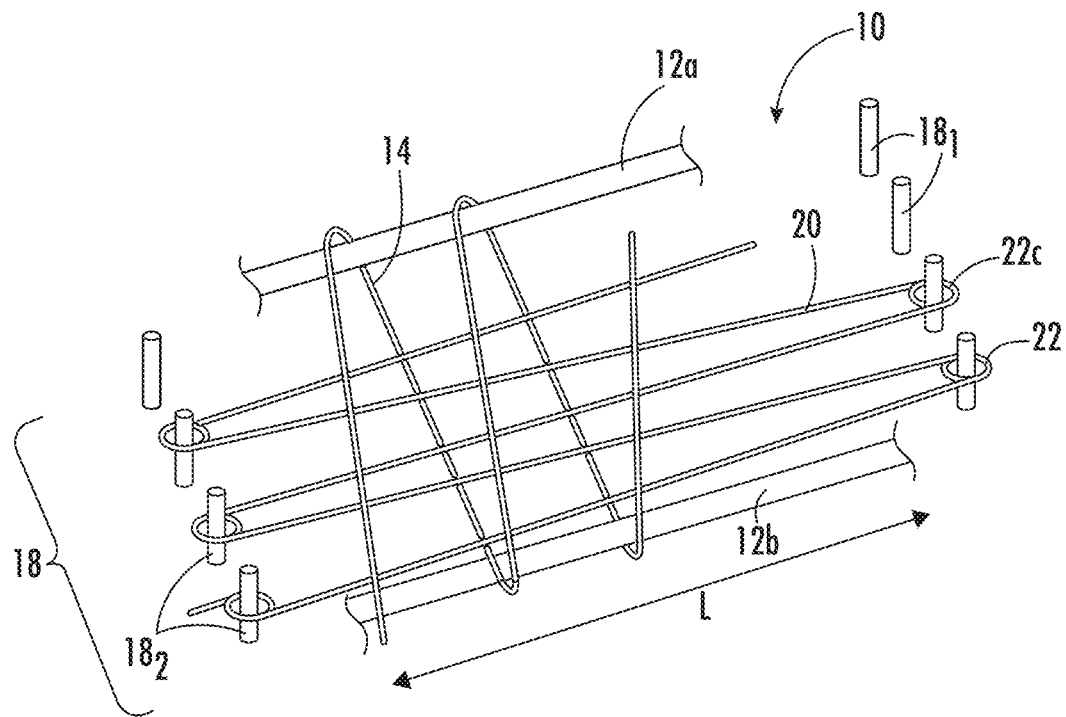
FIG. 8B is a top side perspective view schematic illustration of the example method illustrated in FIG. 8A.
Figure 20B:
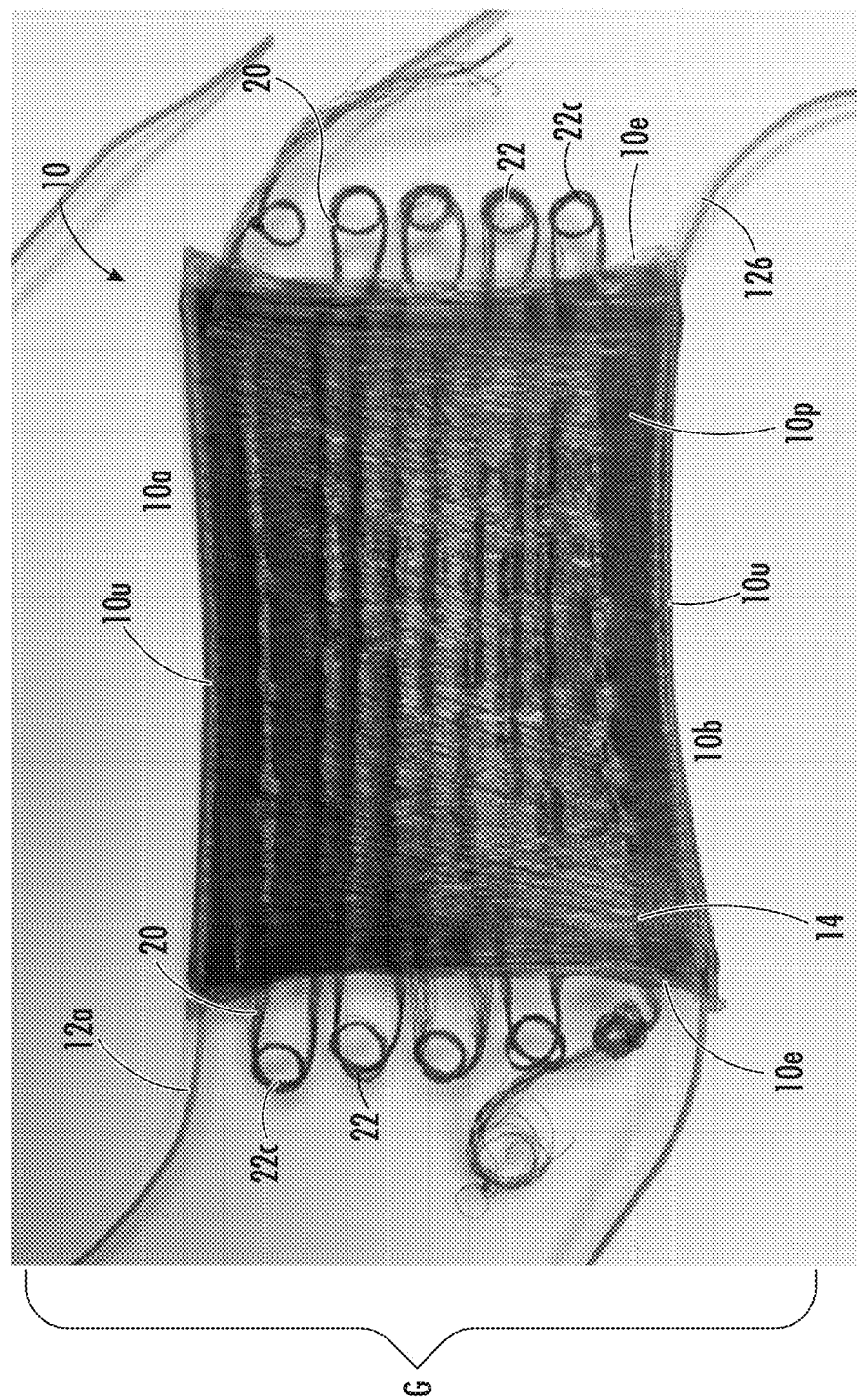
FIG. 20B is a photograph of a prototype medical patch illustrated in FIG. 20A.

As illustrated in FIGS. 8A and 8B, in some embodiments, the plurality of spaced apart posts 18 can reside within the open medial space 16 extending between the first support 12a and second support 12b, but can be spaced laterally apart outside the length (L) of the supports 12a, 12b, such that the plurality of spaced apart posts 18 reside outside one or more outer edges 10e of the medical construct 10 (see, e.g., FIGS. 20A-20B).

Referring back to FIGS. 7A and 7B, in some embodiments, the looping of the biocompatible fiber and/or yarn 20 about the plurality of spaced apart posts 18 may form an open semi-circular loop 22o (see also, e.g., FIGS. 19A-19F).

As shown in FIGS. 8A and 8B, in some embodiments, the looping of the biocompatible fiber and/or yarn 20 may form a closed-circle loop 22c (see also, e.g., FIGS. 20A-20B). The loops 22 formed (open semi-circular loop 22o or closed-circle loop 22c) are at positions corresponding to one or more of the respective spaced apart posts 18.

A variety of different patterns may be formed by looping the continuous length collagen fiber 14 and/or biocompatible fiber and/or yarn 20 about the first and second pluralities of posts 18₁, 18₂. Exemplary non-limiting looping patterns that may be formed are shown in FIGS. 19A-19F (crisscross/zig-zag) and FIGS. 20A-20B (substantially parallel lines). The term "substantially" with respect to these fiber and/or yarn lines means that there can be a +/−15% variation between adjacent longitudinally extending lengths that terminate at the loops 22.

Figure 9:
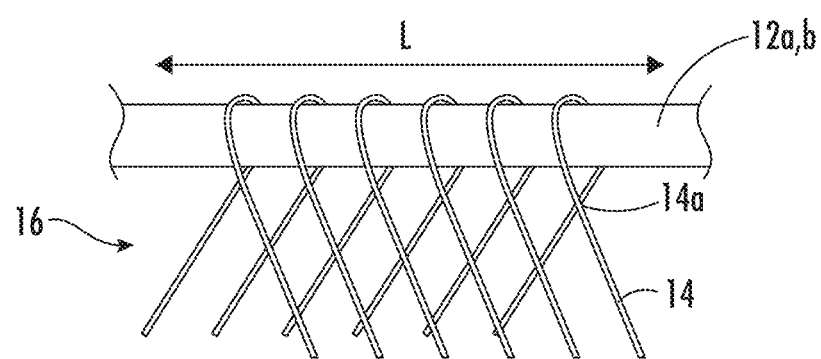
FIG. 9 is an enlarged partial view schematic illustration showing an example method of forming a medical construct according to embodiments of the present invention.

The sequence for winding the continuous length collagen fiber 14 about the first and second supports 12a, 12b may be done in a number of different ways. For example, referring to FIG. 9, in some embodiments, the continuous length collagen fiber 14 may be wound about the first support 12a in a range of about 345 degrees to about 360 degrees such that adjacent lengths of the continuous length collagen fiber 14 abut (14a) proximate the first support 12a. The continuous length collagen fiber 14 may then be wound about the second support 12b across the open medial space 16 extending between the first and second supports 12a, 12b. The continuous length collagen fiber 14 may then be wound about the second support 12b in a range of about 345 degrees to about 360 degrees such that adjacent lengths of the continuous length collagen fiber 14 abut proximate the second support 12b. The continuous length collagen fiber 14 may be wound back across the open medial space 16 to the first support 12a. This winding sequence can be repeated a plurality of times over at least a portion of the length (L) of the first and second supports 12a, 12b.

Figure 10:
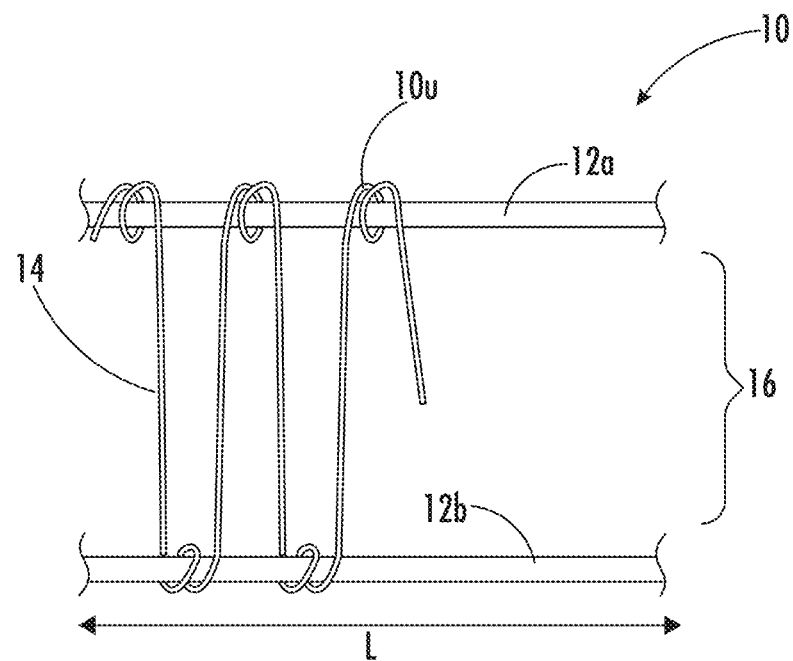
FIG. 10 is a schematic illustration showing an example method of forming a medical construct according to embodiments of the present invention.

As shown in FIG. 10, in some embodiments, the continuous length collagen fiber 14 may be wound in a similar winding sequence, but the continuous length collagen fiber 14 may be wound about the first and second supports 12a, 12b greater than 360 degrees, e.g., 720 degrees.

Similar to winding sequences discussed above, utilizing this winding sequence can result in a medical construct 10 with uncut outer edges 10u. Again, having a medical construct 10 with uncut outer edges 10u eliminates fraying which may improve the properties of the medical construct 10, such as, e.g., tensile strength.

Figure 11:
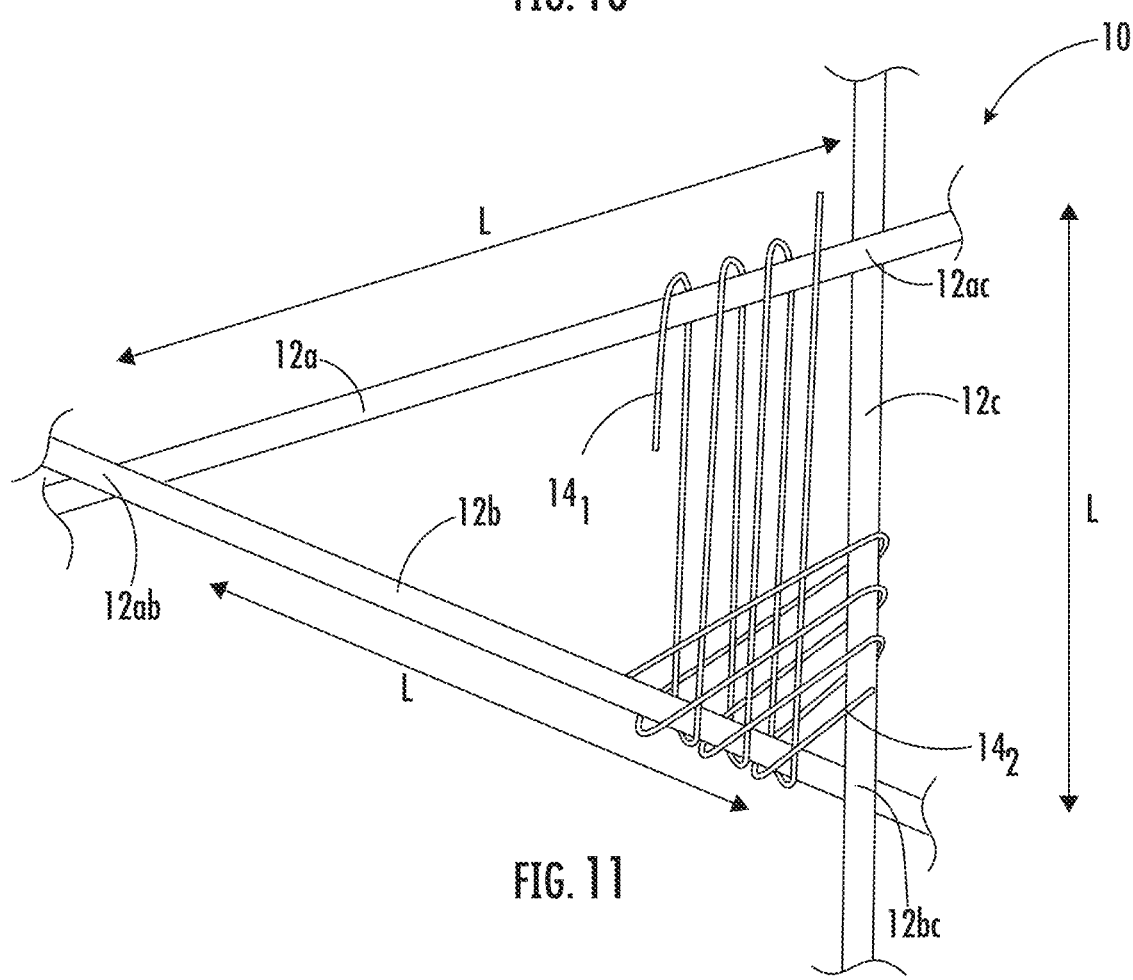
FIG. 11 is a schematic illustration showing an example method of forming a medical construct according to embodiments of the present invention.

Referring now to FIG. 11, in some embodiments, a medical construct 10 can be formed by winding the at least one continuous length collagen fiber 14 (shown as two separate at least one continuous length collagen fibers 14₁, 14₂) about a first support 12a, second support 12b, and third support 12c. The first, second and third supports 12a, 12b, 12c are oriented such that each of the first, second, and third supports 12a, 12b, 12c adjacently cross the other two supports at a point along the length (L) of each support 12a, 12b, 12c, such as, for example, at points 12ab, 12ac, and 12bc. The winding can be carried out to wind the continuous length collagen fiber 14₁,14₂ about each of the first, second, and third supports 12a, 12b, and 12c. In the embodiments that include a third support 12c, the medical construct 10 formed may be a planar triangular medical construct.

Figure 12:
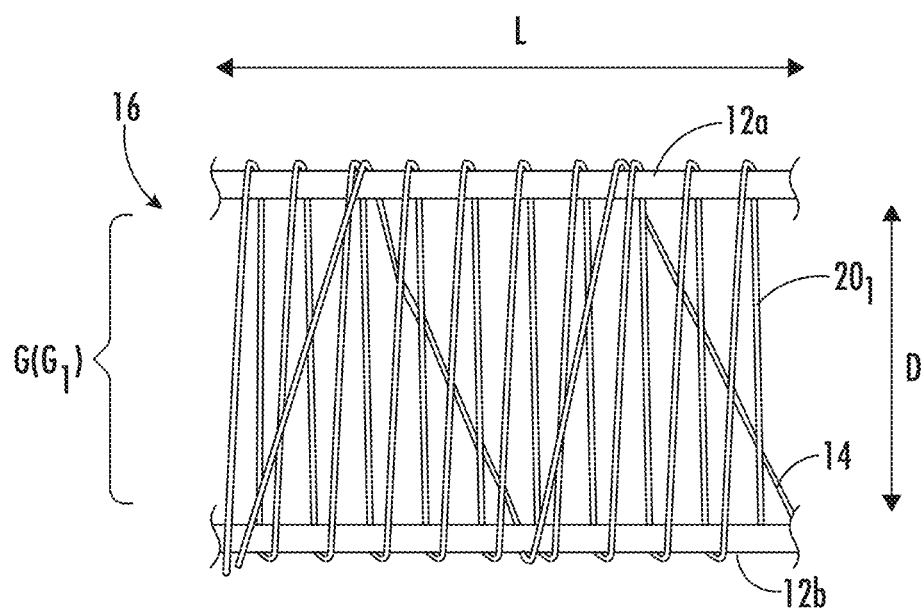
FIG. 12 is a schematic illustration showing an example method of forming a medical construct according to embodiments of the present invention.

Referring now to FIG. 12, similar to methods described above, a first support 12a and second support 12b are provided. Each support 12a, 12b has a length (L) extending in a longitudinal direction. The first and second supports 12a, 12b can be spaced apart from each other a distance (D) with an open medial space 16 extending laterally between the two supports 12a, 12b. The medical construct 10 may be formed by winding at least one biocompatible fiber and/or yarn 20₁ across the open medial space 16 and about the length (L) of the first and second supports 12a, 12b. The winding of the at least one biocompatible fiber and/or yarn 20₁ may form a fiber grid (G).

At least one continuous length collagen fiber 14 can be then wound a plurality of times about a length (L) of the fiber grid (G) and about the length (L) of the first and second supports 12a, 12b. The medical construct 10 formed can include the fiber grid (G) based, at least in part, on the winding step.

By way of example, at least one biocompatible fiber and/or yarn 20₁ is wound across the open medial space 16 and about the first support 12a. The biocompatible fiber and/or yarn 15₁ is next wound back across the open medial space 16 and about the second support 12b. The winding of the biocompatible fiber and/or yarn 20₁ is repeated across the open medial space 16 and about the first support 12a and the second support 12b a plurality of times over at least a portion of the length (L) of each support 12a, 12b forming a fiber grid (G). At least one continuous length collagen fiber 14 is then wound a plurality of times about a length (L) of the fiber grid (G). The medical construct 10 is formed comprising the fiber grid (G) and a plurality of overlying layers 13n of the continuous length collagen fiber 14 based, at least in part, on the winding.

In some embodiments, the biocompatible fiber and/or yarn 20₁ may comprise at least one continuous length collagen fiber 14. The winding across the open medial space 16 provides adjacent directly contacting layers of the continuous length collagen fibers 14 (and/or biocompatible fiber and/or yarn 20₁) between the first and second supports 12a, 12b. The medical construct 10 may comprise an integrated collagen fiber phase (e.g., annealed, bound, and/or stuck together) resulting in a solid construct that may have improved mechanical properties, such as, for example, improved tensile strength.

In some embodiments, the at least one biocompatible fiber and/or yarn 20₁ may be arranged parallel to the longitudinal axis of at least one of the supports 12a, 12b. In other embodiments, the at least one biocompatible fiber and/or yarn 20₁ may be arranged perpendicular relative to a longitudinal axis of at least one of the first and second supports 12a, 12b.

Figure 13:
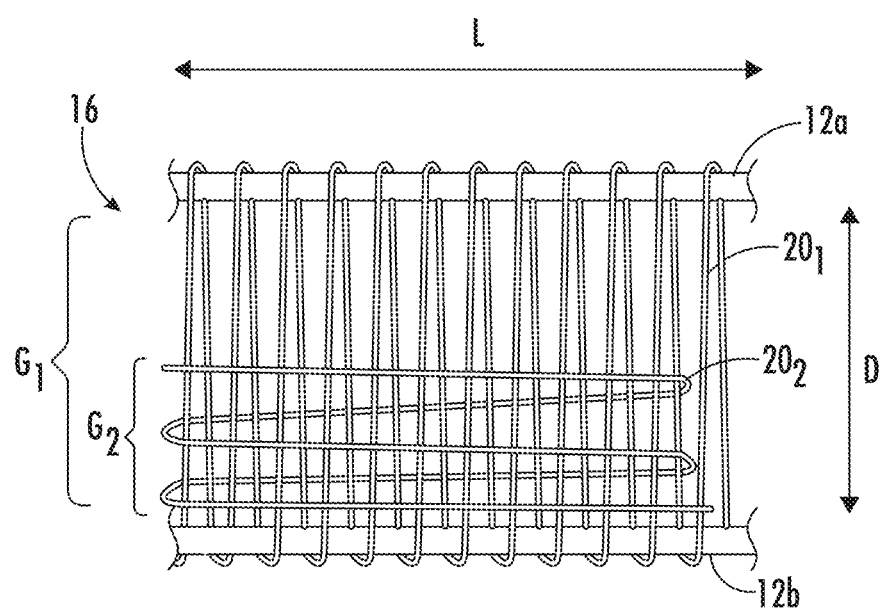
FIG. 13 is a schematic illustration showing an example method of forming a medical construct according to embodiments of the present invention.

In some embodiments, the fiber grid (G) is a first fiber grid ($G_1$). In some embodiments, a second at least one biocompatible fiber and/or yarn 20₂ may be wound about the first fiber grid ($G_1$). As shown in FIG. 13, in some embodiments, the second at least one biocompatible fiber and/or yarn 20₂ may be arranged over and under the first fiber grid ($G_1$) forming a second fiber grid ($G_2$). The second fiber grid ($G_2$) may become an integrated part of the medical construct 10 (see, e.g., FIGS. 21A-21B).

Figure 14:
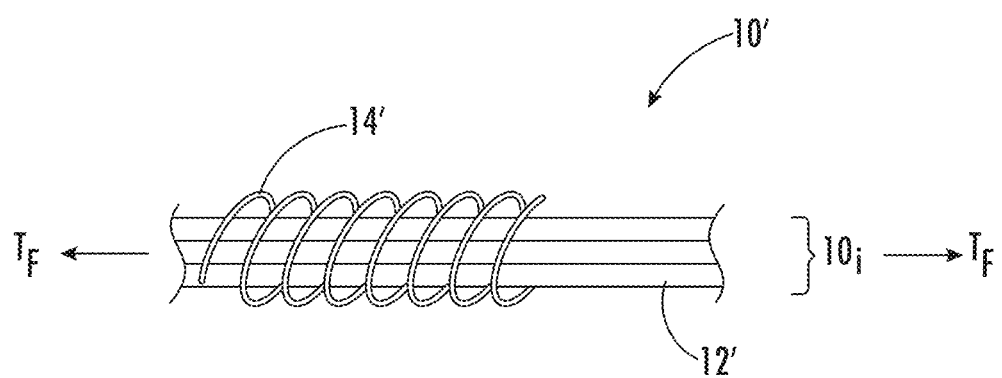
FIG. 14 is a schematic illustration showing an example method of forming a medical construct according to embodiments of the present invention.

FIG. 14 illustrates another example method of forming a medical construct 10' according to additional embodiments of the present invention. A flexible inner core 10i may comprise a plurality of longitudinally extending elongate parallel synthetic collagen fibers 12'. The flexible inner core 10i may be held in tension ($T_F$) while at least one continuous length synthetic collagen fiber 14' may be wound a plurality of revolutions about the flexible inner core 10i. The continuous length synthetic collagen fiber 14' may be wound so that the continuous length synthetic collagen fiber 14' has at least one defined pitch and/or fiber angle that is offset to a longitudinal axis of the flexible inner core 10i. The medical construct 10' formed may be a flexible suture construct comprising the flexible inner core 10i and the continuous length synthetic fiber 14' based, at least in part, by the winding.

Figure 21A:
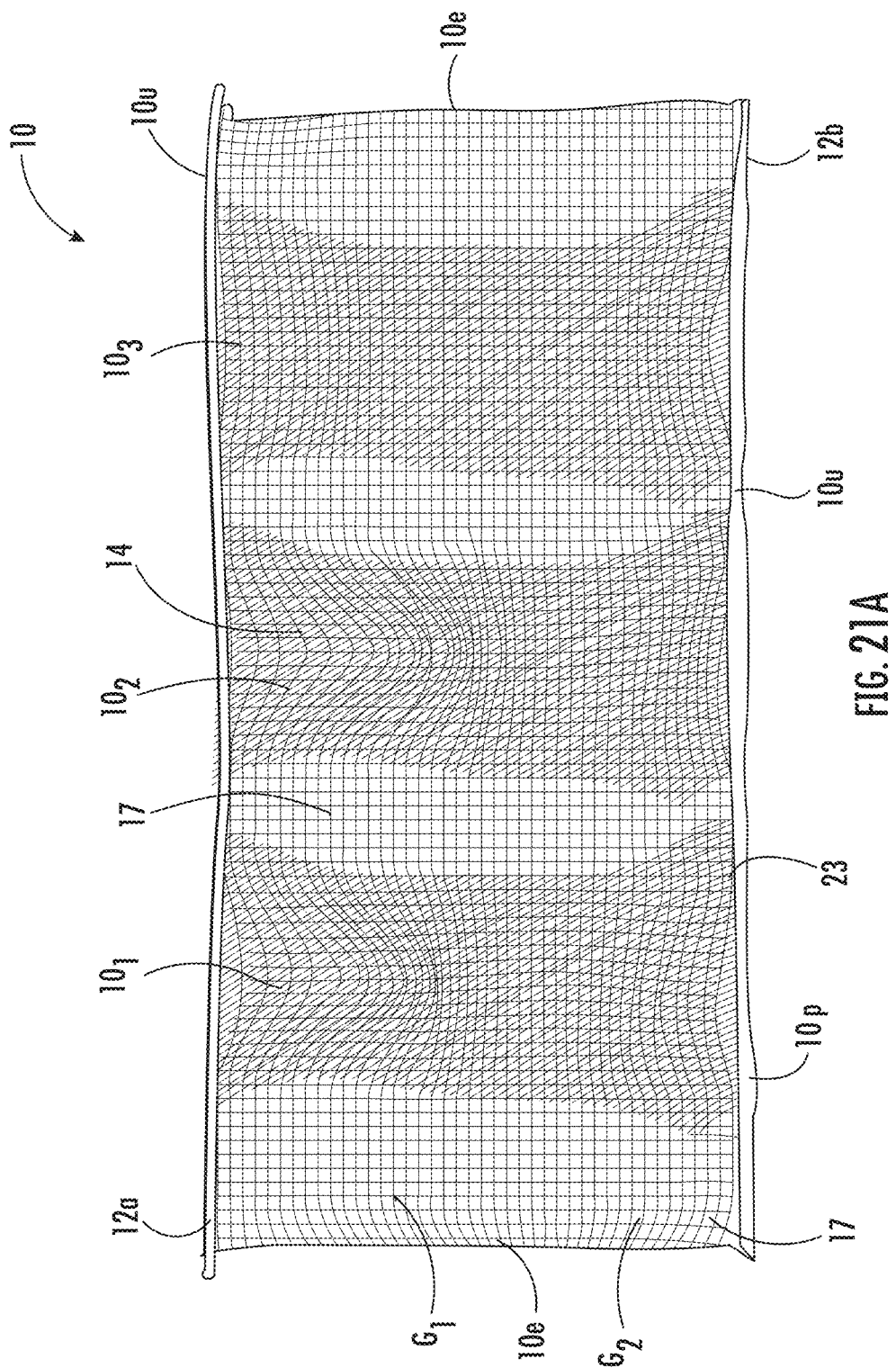
FIG. 21A is a top view image of an example medical patch according to embodiments of the present invention.
Figure 21B:
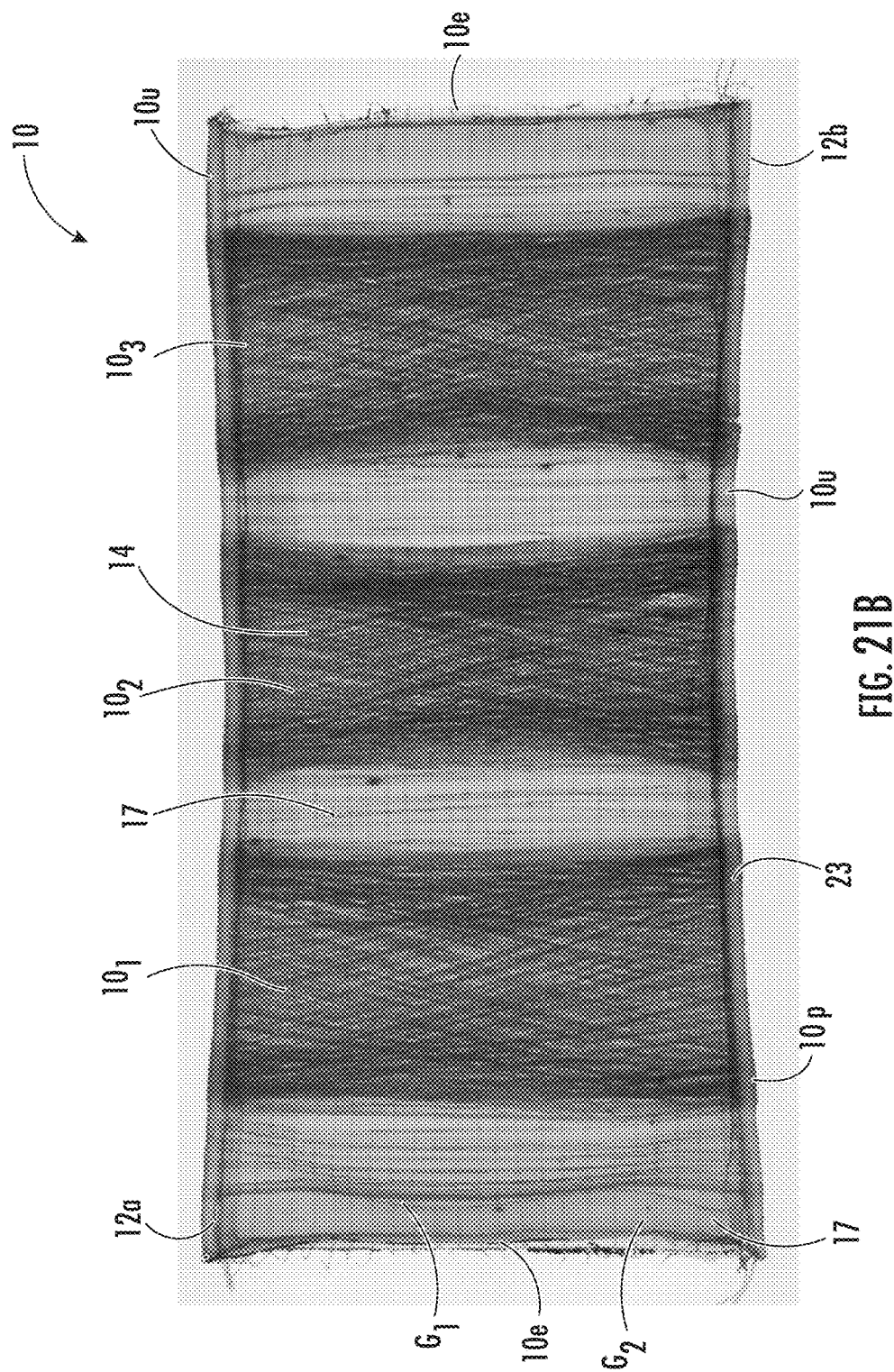
FIG. 21B is a photograph of a prototype medical patch illustrated in FIG. 21A.

In some embodiments, the methods may include adding a polymeric film 17, such as acrylate, to the medical construct 10 (see, e.g., FIGS. 21A-21B). The polymeric film 17 may refer to a thin layer of collagen gel that has dried. The polymeric film 17 is typically present in a thickness that is about 5 µm and about 200 µm. The polymeric film 17 may be permeable and flexible and optically transmissive, e.g., translucent or transparent, or may be opaque. Several layers of the gel can be applied to generate the desired film 17 thickness or coverage. The color or transmissive characteristics of the polymeric film 17 may change when hydrated. The polymeric film 17 can infuse into, migrate and/or bond to wound (dry) collagen fiber(s) 14 and/or biocompatible fiber(s) and/or yarn(s) 20 to form a collagen fiber laminate. The polymeric gel/film 17 is not required, but where used can provide a smooth (and typically a substantially constant diameter) surface over or under the continuous length collagen fiber 14 and/or biocompatible fiber and/or yarn 20.

Optionally, a collagen gel can be placed onto the first and second supports 12a, 12b and the gel can dry to form a film 17 on the outer surface of the supports 12a, 12b before winding the continuous length collagen fiber 14 and/or biocompatible fiber and/or yarn 20 about the supports 12a, 12b. The film 17 can be dried or allowed to dry on the supports 12a, 12b. As the at least one continuous length collagen fiber 14 and/or biocompatible fiber and/or yarn 20 is wound about the supports 12a, 12b, a soluble collagen can be applied (e.g., wrapped, painted, sprayed, dripped and the like) onto the continuous length collagen fiber 14, biocompatible fiber and/or yarn 20, and/or supports 12a, 12b so that the continuous length collagen fiber 14 and/or biocompatible fiber and/or yarn 20 become wet while one or more layers are wound.

In some embodiments, the winding can be carried out to create multiple adjacent overlying layers 13n of the continuous length collagen fiber 14. The adjacent layers can be coextensive for at least a major portion of a length (L) of the medical construct 10. A liquid or gel comprising soluble collagen fiber(s) may be placed onto the continuous length collagen fiber 14 to cover at least the outer surface of the medical construct 10 in a collagen film 17.

Figure 15:
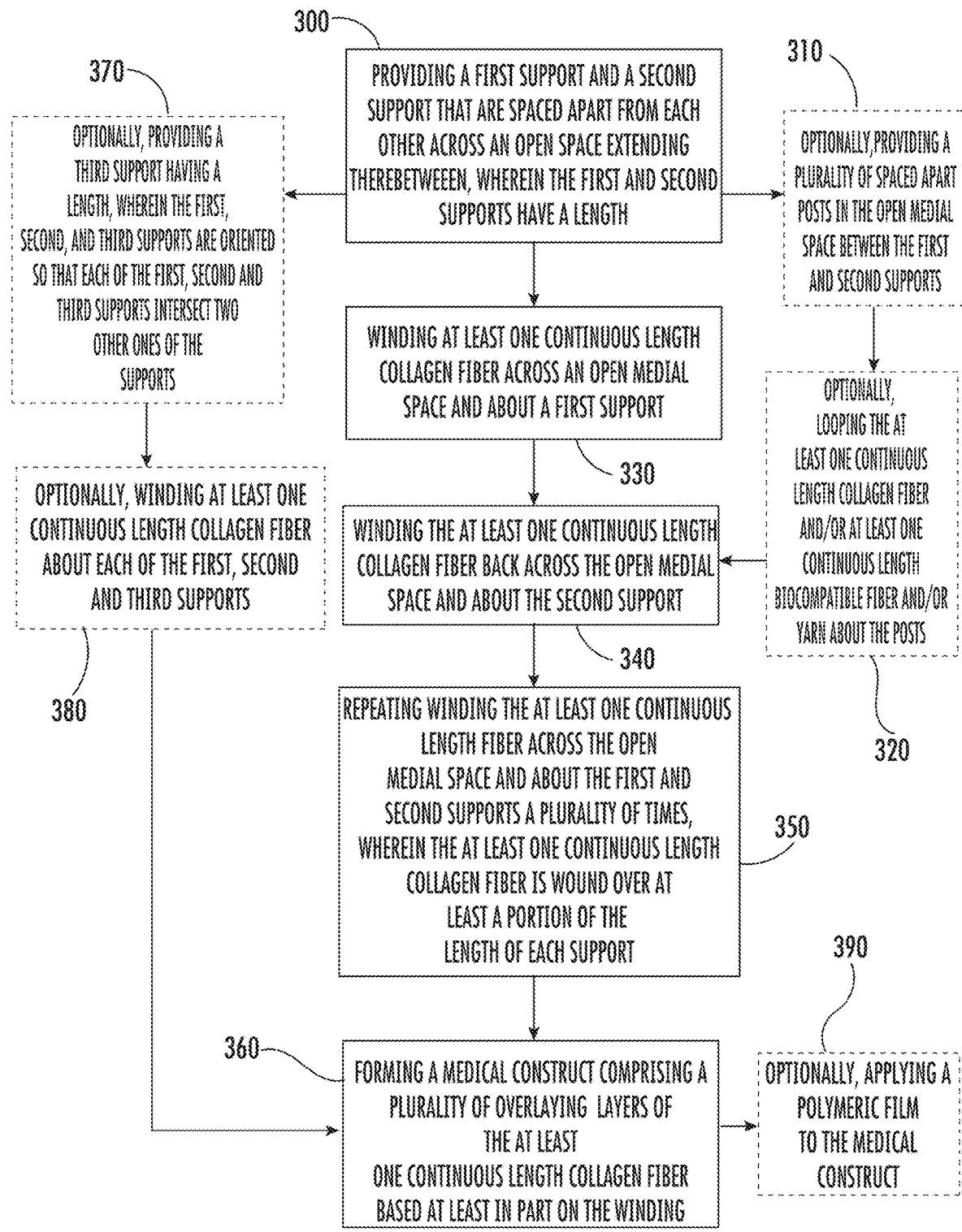
FIG. 15 is a flow chart of example operations that can be used to fabricate a medical construct according to embodiments of the present invention.

FIG. 15 is a flow chart of operations that may be used to carry out some of the embodiments of the present invention discussed above. In some embodiments, a first support and a second support are provided. The first and second supports are spaced apart from each other across an open space extending therebetween, and the first and second supports have a length (block 300).

Optionally, a plurality of spaced apart posts may be provided in the open medial space between the first and the second supports (block 310). Optionally, the at least one continuous length collagen fiber and/or at least one continuous length biocompatible fiber and/or yarn or a different at least one continuous length collagen fiber may be optionally looped about the plurality of posts (block 320).

At least one continuous length collagen fiber may be wound across an open medial space and about the first support (block 330). The at least one continuous length collagen fiber may then be wound back across the open medial space and about the second support (block 340). Winding the at least one continuous length fiber across the open medial space and about the first and second supports may be repeated a plurality of times over at least a portion of the length of each support (block 350). A medical construct may be formed comprising a plurality of overlying layers of the at least one continuous length collagen fiber based, at least in part, on the winding (block 360).

Optionally, in some embodiments, a third support having a length may be provided, wherein the first, second, and third supports are oriented so that each of the first, second, and third supports intersect two other ones of the support (block 370). The at least one continuous length collagen fiber may be optionally wound about each of the first, second, and third supports (block 380).

In some embodiments, a polymeric film can be optionally applied to the medical construct (block 390).

Figure 16:
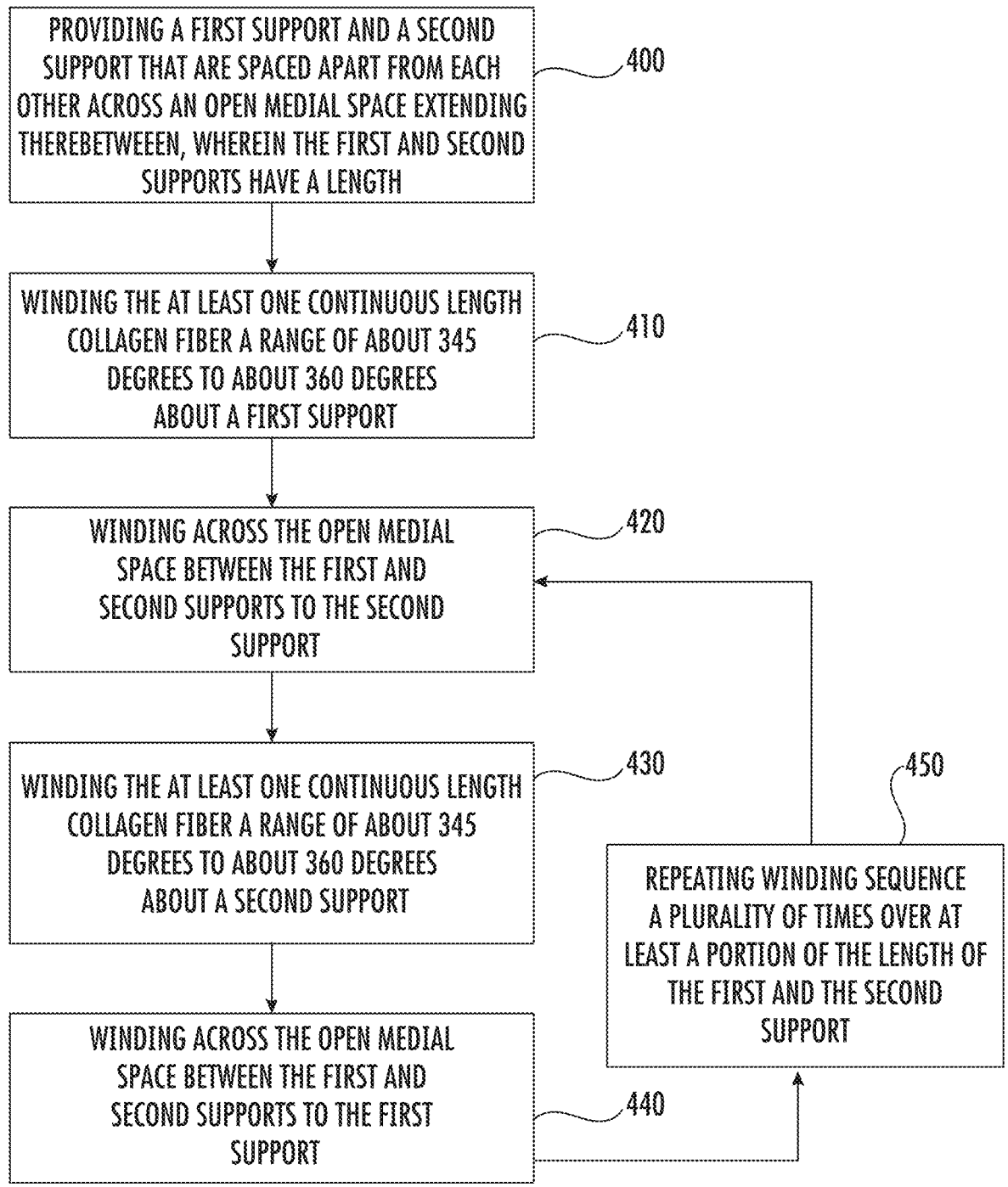
FIG. 16 is a flow chart of example operations that can be used to fabricate a medical construct according to embodiments of the present invention.

FIG. 16 is a flow chart of operations that may be used to carry out embodiments of the present invention. In some embodiments, a first support and a second support may be provided. The first and second supports are spaced apart from each other across an open medial space extending therebetween, wherein the first and second supports have a length (block 400). A winding sequence may comprise first winding at least one continuous length collagen fiber a range of about 345 degrees to about 360 degrees about the first support (block 410). The at least one continuous length collagen fiber may be then wound across the open medial space extending between the first and the second supports to the second support (block 420). Next, the at least one continuous length collagen fiber may be wound a range of about 345 degrees to about 360 degrees about the second support (block 430). Finally, the at least one continuous length collagen fiber may be wound back across the open medial space between the first support and second support to the first support (block 440). This winding sequence may be repeated a plurality of times over at least a portion of the length of the first support and the second support (block 450).

Figure 17:
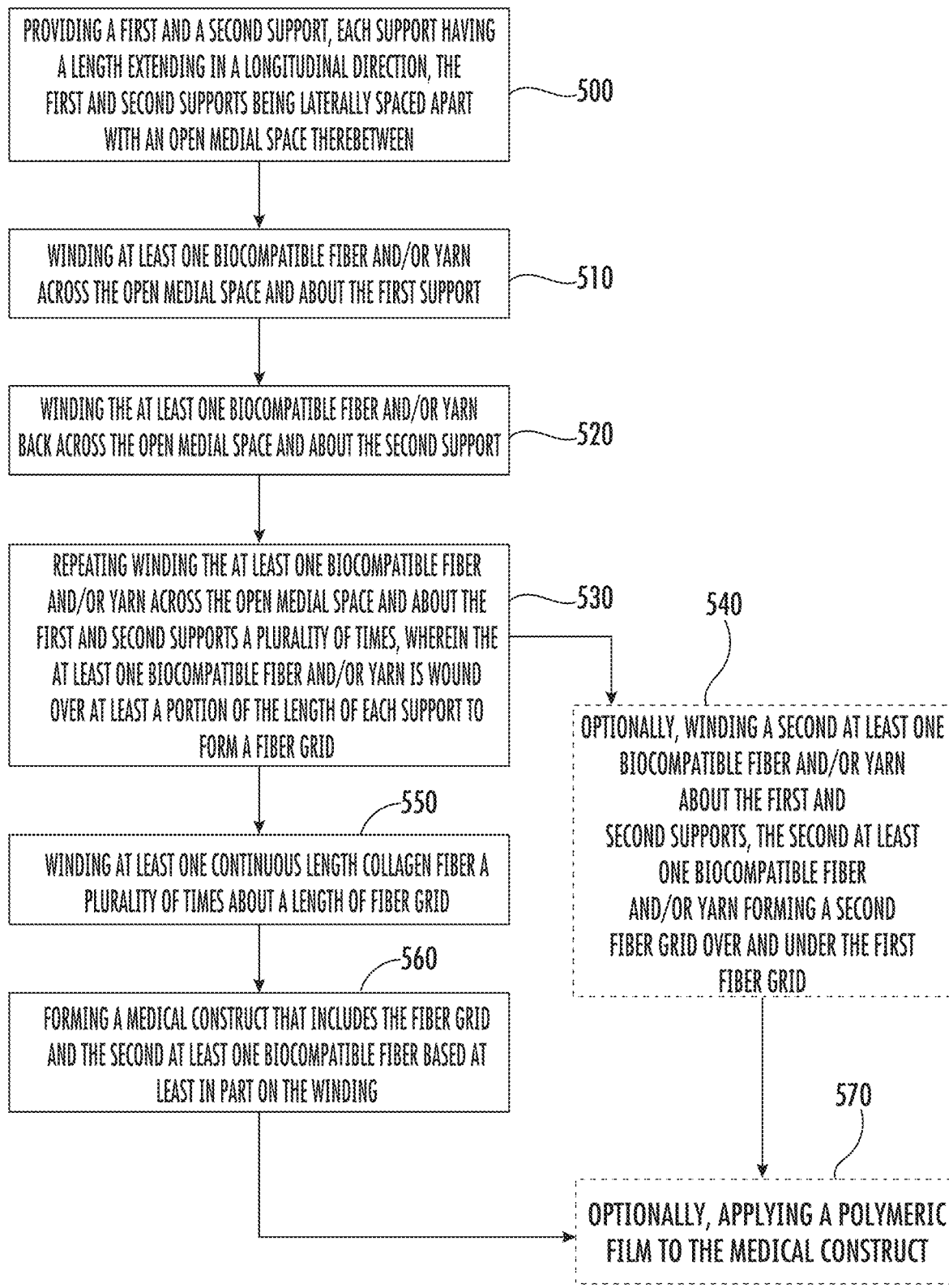
FIG. 17 is a flow chart of example operations that can be used to fabricate a medical construct according to embodiments of the present invention.

FIG. 17 is a flow chart of operations that may be used to carry out embodiments of the present invention. In some embodiments, a first and a second support may be provided, each support having a length extending in a longitudinal direction, the first and second supports being laterally spaced apart with an open medical space therebetween (block 500). At least one biocompatible fiber and/or yarn may be wound across an open medial space and about the first support (block 510). The at least one biocompatible fiber and/or yarn may next be wound back across the open medial space and about the second support (block 520). Winding the at least one biocompatible fiber and/or yarn across the open medial space and about the first and second supports may be repeated a plurality of times over at least a portion of the length of each support to form a fiber grid (block 530).

Optionally, a second at least one biocompatible fiber and/or yarn may be wound about the first support and the second support. The second at least one biocompatible fiber and/or yarn can form a second fiber grid over and under the first fiber grid (block 540).

At least one continuous length collagen fiber may be then wound a plurality of times about a length of the fiber grid(s) (block 550). A medical construct may be formed comprising a plurality of overlying layers of the at least one continuous length collagen fiber based, at least in part, on the winding (block 560). In some embodiments, a polymeric film can be optionally applied to the medical construct (block 570).

Figure 18:
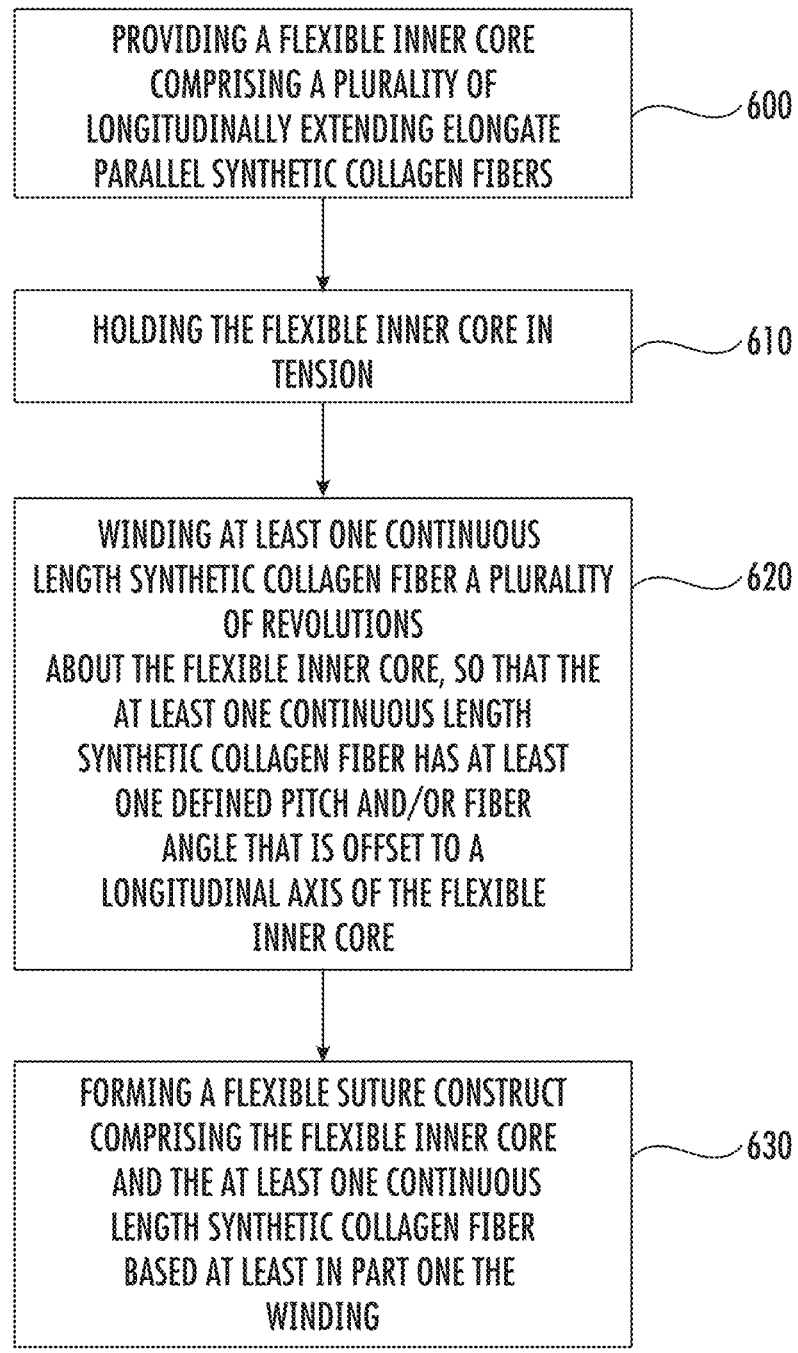
FIG. 18 is a flow chart of example operations that can be used to fabricate a medical construct according to embodiments of the present invention.

FIG. 18 is a flow chart of operations that may be used to carry out embodiments of the present invention. In some embodiments, a flexible inner core comprising a plurality of longitudinally extending elongate parallel synthetic collagen fibers may be provided (block 600). The flexible inner core may be held in tension (block 610). At least one continuous length synthetic collagen fiber may be wound a plurality of revolutions about the flexible inner core, so that the at least one continuous length synthetic collagen fiber has at least one defined pitch and/or fiber angle that is offset to a longitudinal axis of the flexible inner core (block 620). A flexible suture construct may be formed comprising the flexible inner core and the at least one continuous length synthetic collagen fiber based at least in part on the winding (block 630).

Exemplary medical constructs 10 that can be formed by the methods of manufacturing disclosed above are now provided. In some embodiments, the medical construct 10 may be a planar construct, for example, a medical patch.

Referring now to FIGS. 19A-19F, in some embodiments, the medical patch 10 may have a primary patch body 10*p*. The patch body 10*p* may have a perimeter comprising a first side 10*a* and an opposing second side 10*b*, each side having uncut outer edges 10*u*. Each of the first side 10*a* and second side 10*b* may have an outer edge portion 10*u*. Each outer edge portion 10*u* may have at least one biocompatible fiber, yarn, or suture 12 extending parallel to the first and second sides 10*a*, 10*b*. The medical patch 10 can also include a continuous length collagen fiber 14 which may extend a plurality of times across the patch body 10*p* in a mesh pattern or fiber grid (G). The fiber grid (G) may have a plurality of overlying layers 13*n* that define interstitial spaces 23 (see also, e.g., FIGS. 3A and 3B). The fiber grid (G) may also extend in a range of about 345 degrees to about 360 degrees of an outer surface of the at least one biocompatible fiber, yarn, or suture 12 (see also, e.g., FIG. 9). As a result, the medical construct 10 can have a perimeter with uncut edges 10*u* and ends 10*e*.

In some embodiments, the biocompatible fiber, yarn, or suture 12 has a diameter that is greater than a diameter of the continuous length collagen fiber 14. The biocompatible fiber, yarn, or suture 12 may be formed with a cross-sectional width and/or diameter such as, for example from about 0.1 mm to about 1.5 mm.

Figure 19A:
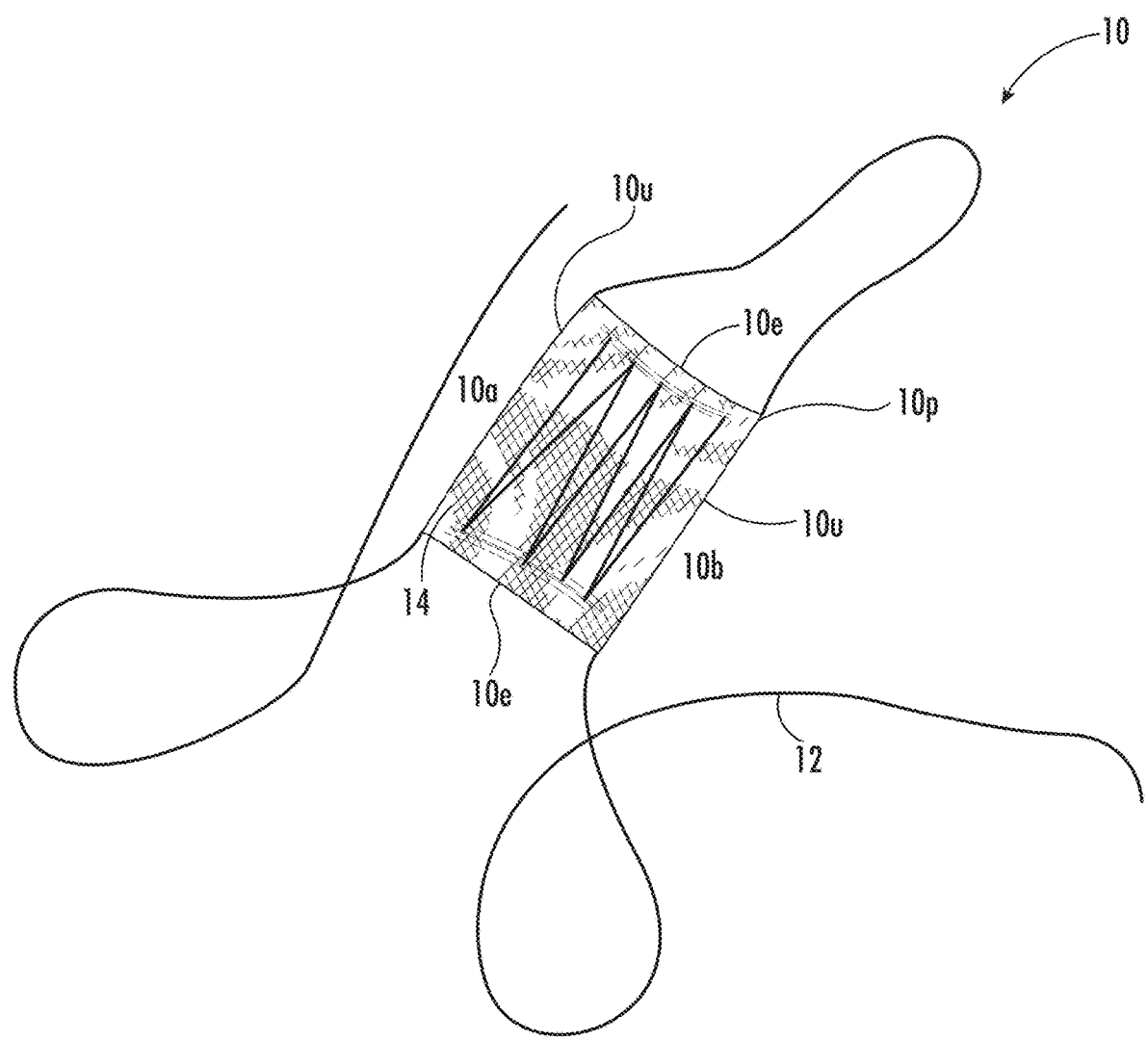
FIG. 19A is a top view image of an example medical patch according to embodiments of the present invention.
Figure 19B:
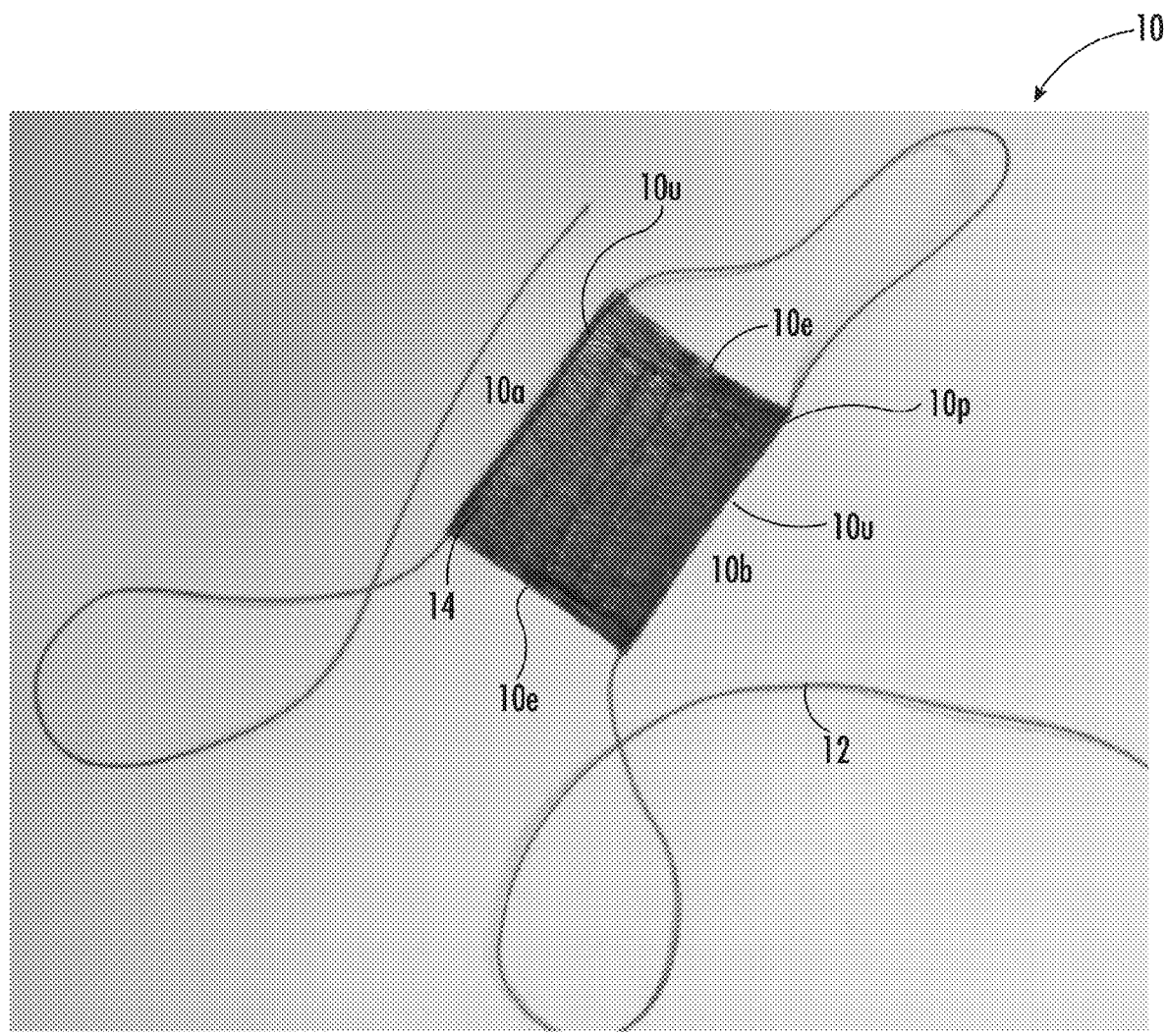
FIG. 19B is a photograph of a prototype medical patch illustrated in FIG. 19A.
Figure 19C:
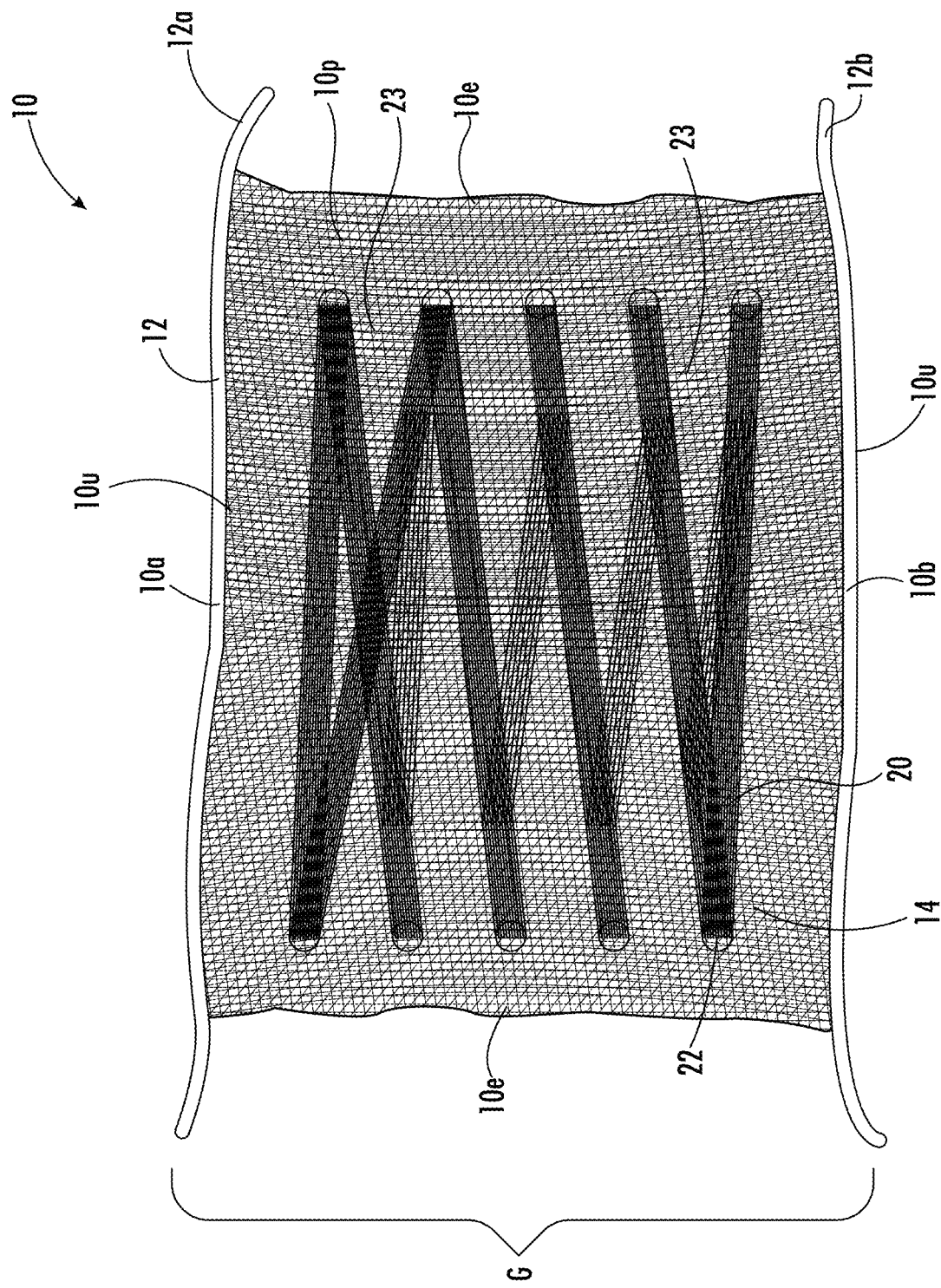
FIG. 19C is an enlarged view image of the example medical patch illustrated in FIG. 19A.
Figure 19D:
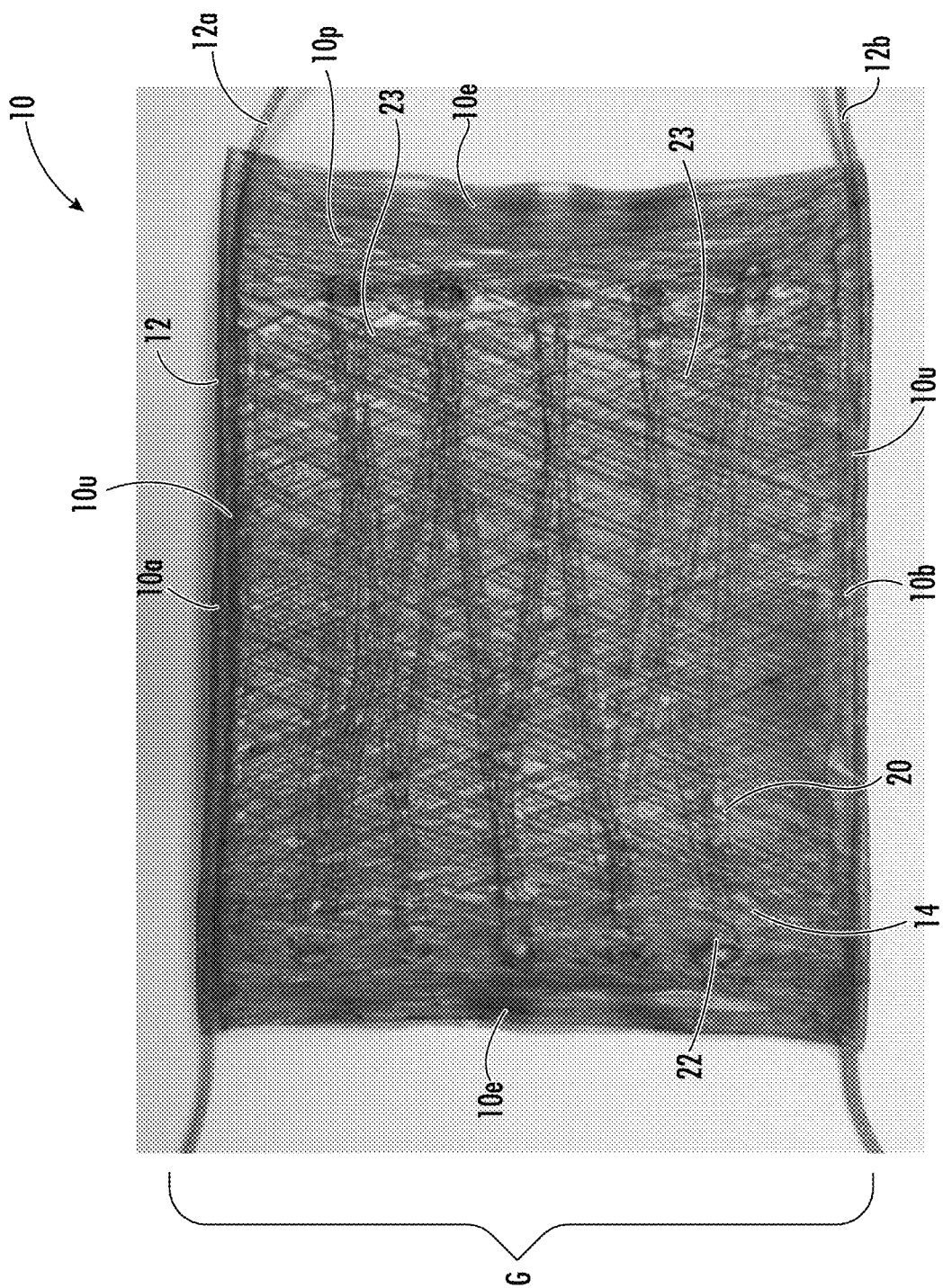
FIG. 19D is a photograph of a prototype medical patch illustrated in FIG. 19C.

In some embodiments, the medical patch 10 may comprise at least one suture anchor aperture 22*s* within the fiber grid (G) (FIG. 19C). The suture anchor aperture(s) 22*s* can have a size greater than the interstitial spaces 23 that can be sized and configured to allow a suture to pass through the patch body 10*p*.

Referring to FIG. 19C, in some embodiments, the medical patch 10 may comprise another biocompatible fiber and/or yarn 20 residing within the patch body 10*p*. The biocompatible fiber and/or yarn 20 may be spaced apart from the outer edges 10*u* of the first and second sides 10*a*, 10*b* of the patch body 10*p*.

Figure 19E:
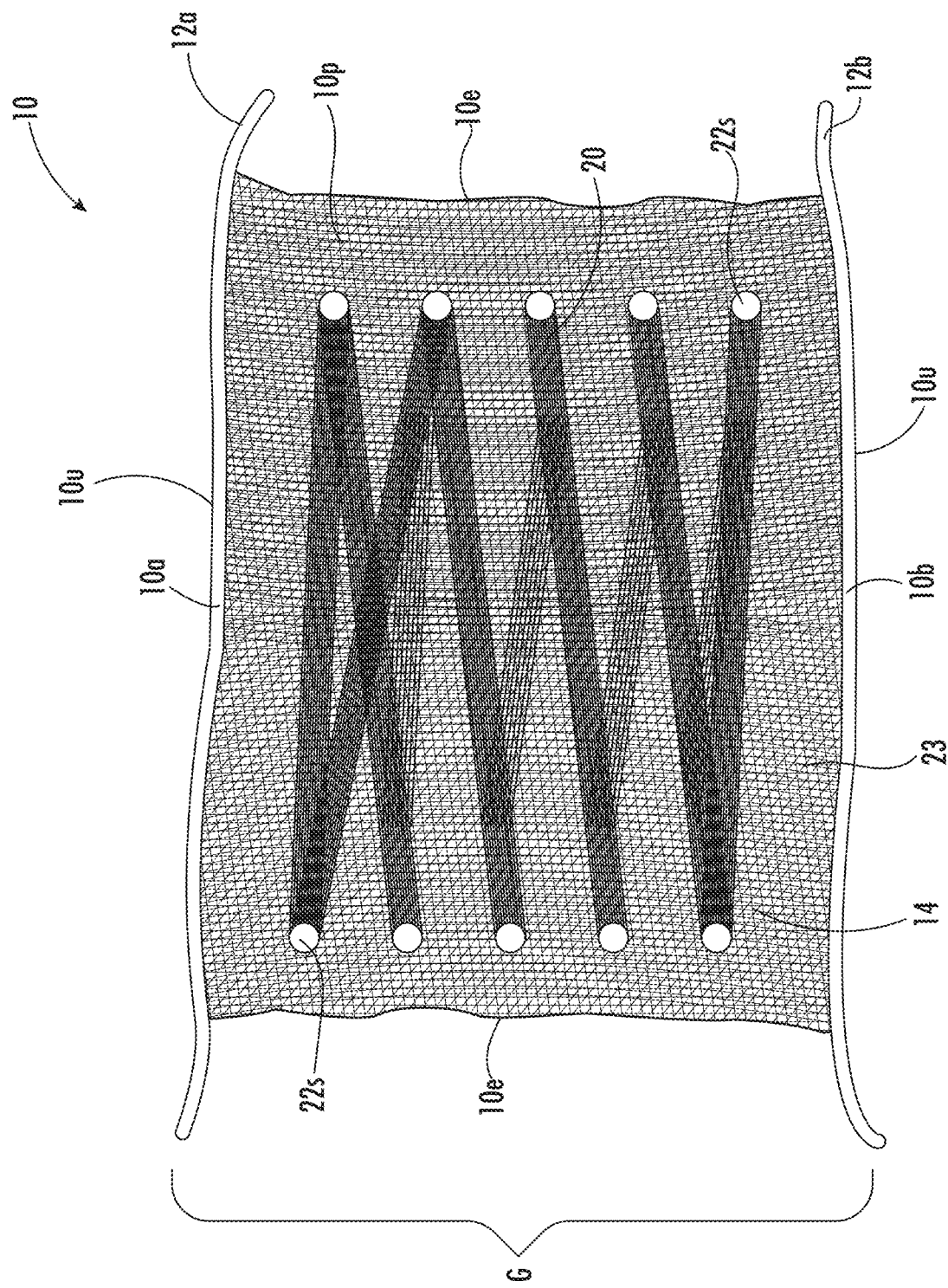
FIG. 19E is a top view image of an example medical patch according to embodiments of the present invention.
Figure 19F:
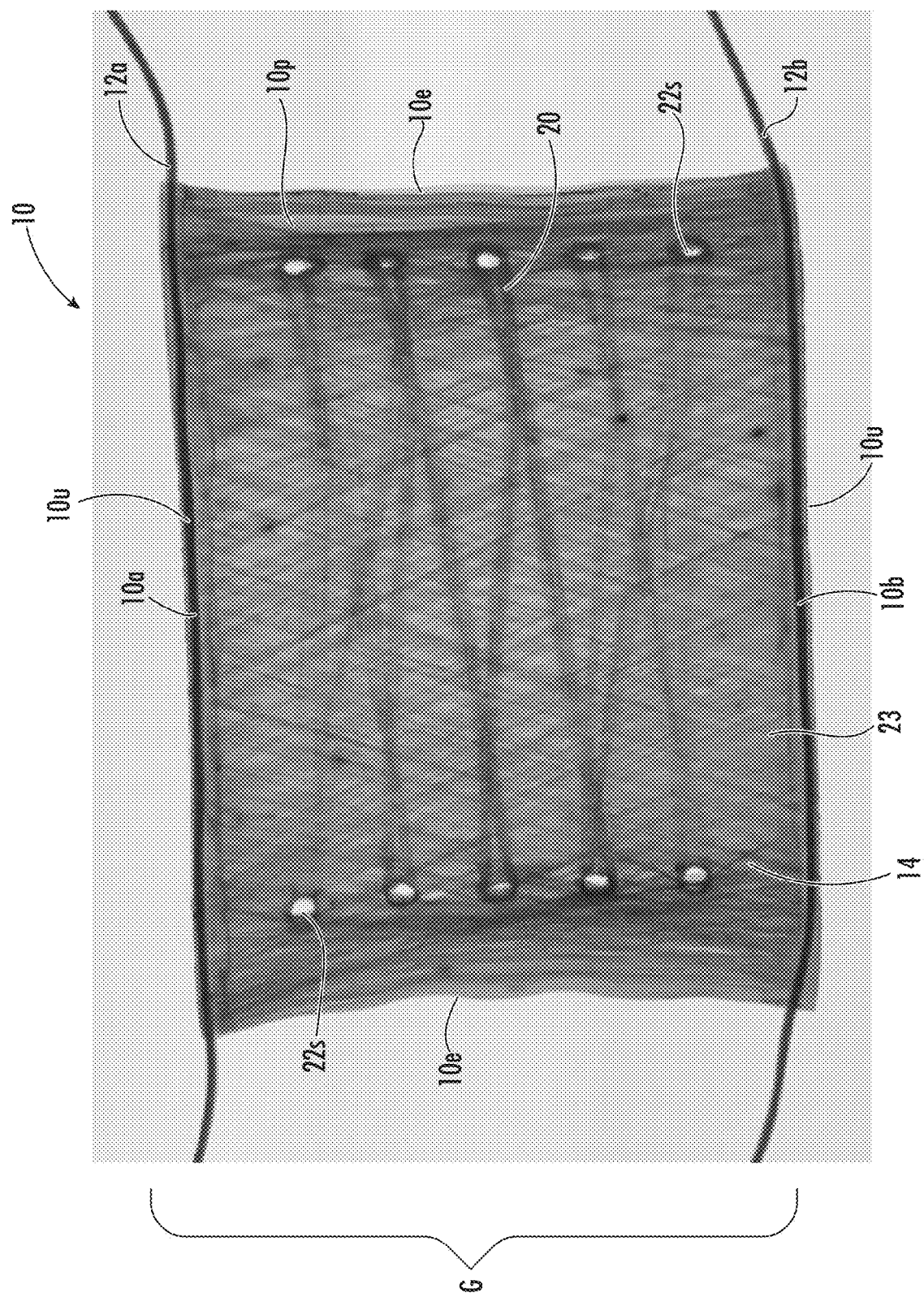
FIG. 19F is a photograph of a prototype medical patch illustrated in FIG. 19E.

Referring to FIGS. 19E, 19F and 20A-20B, in some embodiments, the medical patch 10 may comprise a plurality of loops 22 formed from the at least one biocompatible fiber and/or yarn 20. The loops 22 may extend within or outside the perimeter boundary (i.e., the edges 10*u*, 10*e*) of the patch body 10*p*. In some embodiments, a medical patch 10 may have one or more of the loops 22 residing within the patch body 10*p* that define at least one suture anchor aperture 22*s* (FIGS. 19E and 19F). In other embodiments, a medical patch 10 may have one or more loops 22 that reside outside the patch body 10*p* and have a closed-circle loop 22*c* (FIGS. 20A-20B).

As shown in FIGS. 21A-21B, in some embodiments, the medical patch 10 may further comprise a polymeric film 17 that extends over the interstitial spaces 23. In the embodiments comprising a polymeric film 17, the film 17 cooperates with the continuous length collagen fiber 14 to form an impermeable patch body 10*p*. This impermeable patch body 10*b* can prevent fluid leakage through the medical patch 10 when implanted into the human body.

In some embodiments, multiple medical patches 10 may be formed on the first and second supports 12*a*, 12*b*. For example, FIGS. 21A-21B show three medical patches 10$_1$, 10$_2$, 10$_3$ with integrated grids G$_1$, G$_2$ and supports 12*a*, 12*b* that were formed using the same supports 12*a*, 12*b*.

Figure 22A:
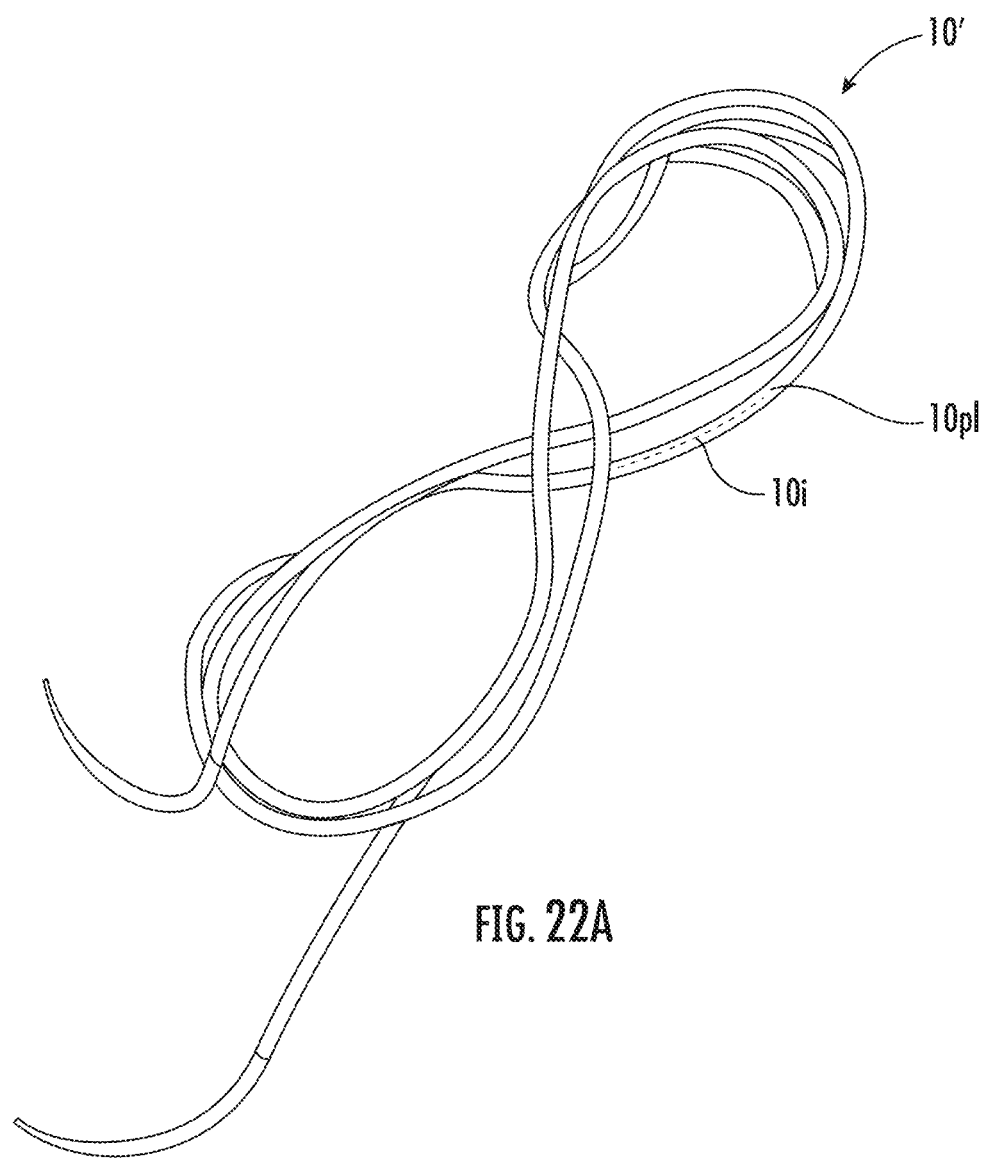
FIG. 22A is a side perspective view image of an example medical suture according to embodiments of the present invention.
Figure 22B:
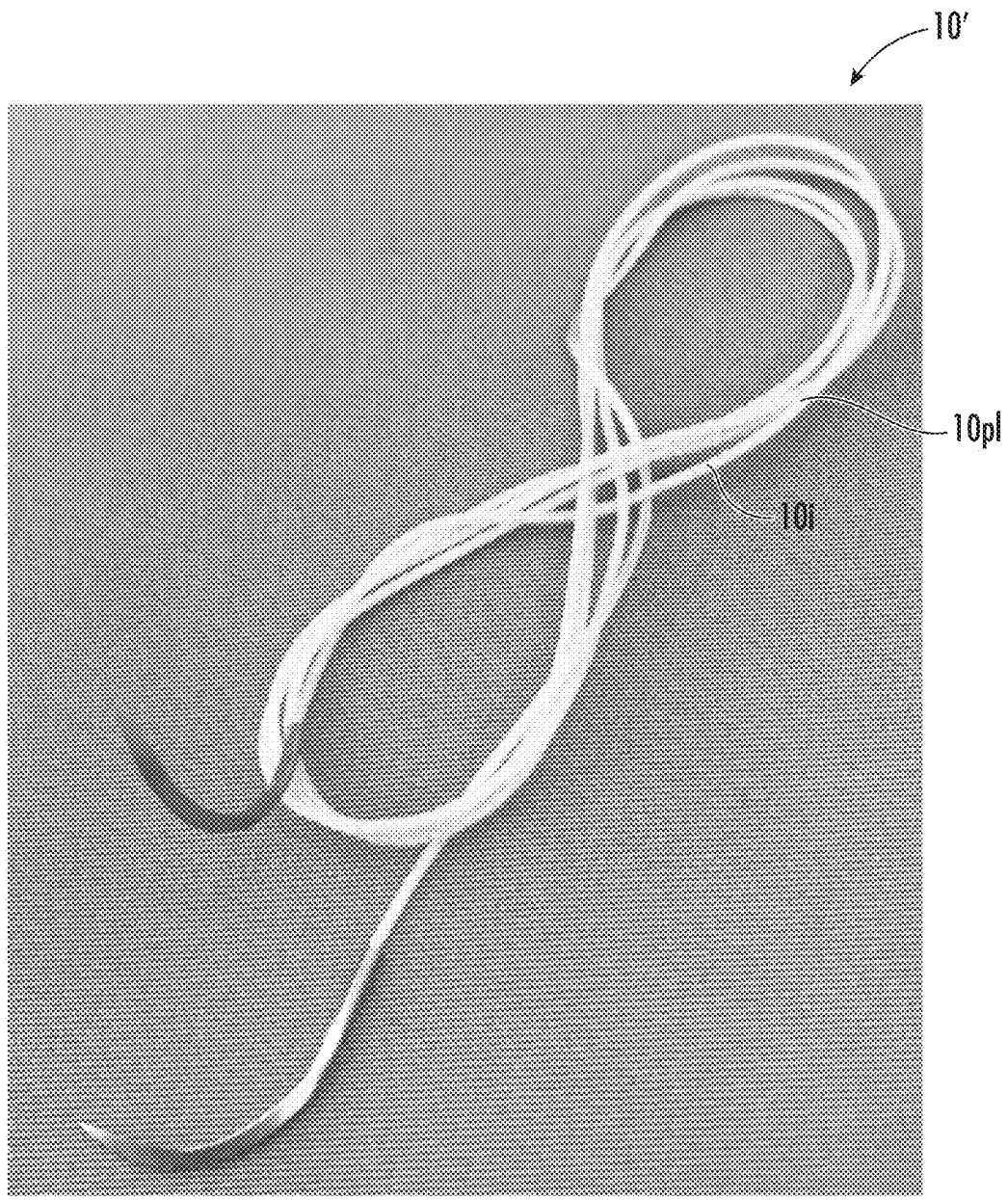
FIG. 22B is a photograph of a prototype medical suture illustrated in FIG. 22A.

FIGS. 22A and 22B illustrate another embodiment of the present invention. As seen in FIGS. 22A-22B, the medical construct 10 may be a medical suture 10'. The medical suture 10' may comprise a cylindrical body 10*p'*. The cylindrical body 10*p'* may comprise a flexible inner core 10*i* (e.g., FIG. 14) of a plurality of longitudinally extending elongate parallel synthetic collagen fibers 14. At least one continuous length synthetic collagen fiber 14 extends a number of revolutions about the cylindrical body 10*p'* and over a length (L) of the cylindrical body 10*p'* at least one defined pitch and/or fiber angle that is offset to a longitudinal axis of the flexible inner core 10*i* to provide an outer surface.

The medical constructs 10 of the present invention can be wound with increased fiber density along certain segments, which can reside at different locations within the medical construct 10. This increased fiber density can provide sufficient rigidity to allow a suture to attach thereto.

The medical construct 10 and/or the collagen fiber(s) 14 can optionally be cross-linked with a suitable polymerizing material, such as, but not limited to, 1-ethyl-3-(3-dimethyl-aminopropyl) carbodiimide (EDC) and/or nordihydroguaiaretic acid (NDGA), or the collagen fiber(s) may be used in the medical construct 10 in a non-cross-linked state. In some embodiments, the cross-linking of the collagen fiber(s) 14 increases the strength of the medical construct 10. In some embodiments, the collagen fiber(s) 14 is not cross-linked during the winding process.

In some embodiments, the collagen fiber(s) 14 can be cross-linked with EDC before the winding about the supports 12a, 12b. In some embodiments, the winding step can be carried out using both (a) one or more uncrosslinked collagen fibers and (b) one or more cross-linked collagen fibers, such as, e.g., one or more EDC cross-linked collagen fibers.

Embodiments of the invention can be used for a number of different medical applications, including, but not limited to, wound bed patches, muscle or organ patches, cardiac patches, valve replacements or repairs, hernia patches, skin patches, burn treatment patches, skin/tissue repair patches or cuffs, blood vessel (artery, vein, and the like) repairs, constructs that can reside about repaired tendon to prevent or inhibit adhesions, and/or constructs for delivery of therapeutic agents.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A medical patch, comprising:
    a patch body comprising a perimeter with a first side and an opposing second side, each of the first and second sides having an outer edge portion, wherein each outer edge portion comprises a first biocompatible fiber and/or yarn extending parallel to the first and second sides;
    at least one continuous length collagen fiber that extends a plurality of times across the patch body in a mesh pattern having a plurality of overlying layers defining interstitial spaces and at least a portion of the at least one continuous length collagen fiber extends in a range of about 345 degrees to about 360 degrees about an outer surface of the at least one first biocompatible fiber and/or yarn of the outer edge portion of the first and second sides; and
    a second biocompatible fiber and/or yarn residing within the patch body between the plurality of overlying layers of the mesh pattern, positioned inwardly and spaced apart from the outer edge portion of the first and second sides.

2. The medical patch of claim 1, wherein the first biocompatible fiber and/or yarn has a diameter that is greater than a diameter of the at least one continuous length collagen fiber.

3. The medical patch of claim 1, further comprising at least one suture anchor aperture in the mesh pattern, wherein the at least one suture anchor aperture has a size greater than the interstitial spaces to thereby allow a suture to pass therethrough.

4. The medical patch of claim 1, further comprising a plurality of loops of the second biocompatible fiber and/or yarn extending between and/or outside the outer edge portions of the first and second sides of the patch body.

5. The medical patch of claim 4, wherein one or more of the plurality of loops reside within the patch body and define at least one suture anchor aperture.

6. The medical patch of claim 4, wherein one or more of the plurality of loops reside outside the patch body and have a closed-circle loop shape.

7. The medical patch of claim 1, wherein the patch body further comprises a third side, the at least one continuous length collagen fiber further extending a plurality of times across the patch body and about the third side of the patch body to form the mesh pattern.

8. The medical patch of claim 1, wherein the patch body further comprises an inner layer comprising the second biocompatible fiber and/or yarn arranged in a fiber grid pattern under the mesh pattern.

\* \* \* \* \*